US009663803B2

(12) United States Patent
Lee et al.

(10) Patent No.: US 9,663,803 B2
(45) Date of Patent: May 30, 2017

(54) GENETICALLY ENGINEERED YEAST CELL CAPABLE OF PRODUCING LACTATE, METHOD OF PRODUCING THE SAME, AND METHOD OF PRODUCING LACTATE BY USING THE CELL

(71) Applicant: Samsung Electronics Co., Ltd., Suwon-si, Gyeonggi-do (KR)

(72) Inventors: Juyoung Lee, Daegu (KR); Changduk Kang, Gwacheon-si (KR); Soyoung Lee, Daegu (KR); Youngkyoung Park, Seoul (KR); Jiyoon Song, Seoul (KR); Seunghyun Lee, Asan-si (KR); Kwangmyung Cho, Seongnam-si (KR)

(73) Assignee: SAMSUNG ELECTRONICS CO., LTD, Suwon-si (KR)

( * ) Notice: Subject to any disclaimer, the term of this patent is extended or adjusted under 35 U.S.C. 154(b) by 65 days.

(21) Appl. No.: 14/541,051

(22) Filed: Nov. 13, 2014

(65) Prior Publication Data

US 2015/0140625 A1 May 21, 2015

(30) Foreign Application Priority Data

Nov. 14, 2013 (KR) ........................ 10-2013-0138359

(51) Int. Cl.
*C12N 9/90* (2006.01)
*C12P 7/56* (2006.01)
*C12N 15/81* (2006.01)

(52) U.S. Cl.
CPC ................ *C12P 7/56* (2013.01); *C12N 15/81* (2013.01); *C12Y 503/01001* (2013.01)

(58) Field of Classification Search
CPC ............ C12N 9/90; C12Y 599/00; C12P 7/56
USPC ........................................................ 435/252.3
See application file for complete search history.

(56) References Cited

U.S. PATENT DOCUMENTS 8,541,208 B1 * 9/2013 Plesch .................. C07K 14/245 435/106
2011/0136195 A1 6/2011 Richards et al.
2011/0262980 A1 10/2011 Soucaille et al.

* cited by examiner

*Primary Examiner* — Maryam Monshipouri
(74) *Attorney, Agent, or Firm* — Leydig, Voit & Mayer, Ltd.

(57) ABSTRACT

A genetically engineered yeast cell capable of producing lactate having increased TPI activity, a method of preparing the yeast cell, and a method of producing lactate by using the yeast cell.

14 Claims, 7 Drawing Sheets

GENETICALLY ENGINEERED YEAST CELL CAPABLE OF PRODUCING LACTATE, METHOD OF PRODUCING THE SAME, AND METHOD OF PRODUCING LACTATE BY USING THE CELL

RELATED APPLICATIONS

This application claims the benefit of Korean Patent Application No. 10-2013-0138359, filed on Nov. 14, 2013, in the Korean Intellectual Property Office, the entire disclosure of which is hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted concurrently herewith and identified as follows: One 68,510 Byte ASCII (Text) file named 716720_ST25.TXT-Revised created on Feb. 2, 2015.

BACKGROUND

1. Field

The present disclosure relates to a genetically engineered yeast cell capable of producing lactate, a method of producing the same, and a method of producing lactate by using the cell.

2. Description of the Related Art

Lactate is an organic acid that is broadly used in various industrial fields, such as food, pharmaceutics, chemicals, and electronics. Lactate is colorless, odorless, and a low-volatile material that dissolves well in water. Lactate is non-toxic to the human body and thus may be used as a flavor agent, a taste agent, or a preserving agent. Also, lactate is an environment-friendly alternative polymer material and a raw material of a polylactic acid (PLA) that is biodegradable plastic.

PLA is a polyester-based resin that is obtained by ring opening polymerization (ROP) of lactide, a dimer which has been converted from lactic acid. PLA may be variously processed to a film, sheet, fiber, plastic, etc. Thus, demands for PLA as bioplastic have recently increased to broadly replace conventional typical petrochemical plastic, such as polyethylene (PE), polypropylene (PP), polyethylene terephthalate (PET), or polystyrene (PS).

Lactate includes both a hydroxyl group and a carboxyl group and thus is highly reactive. Accordingly, lactate is easily converted into industrially important compounds, such as lactate ester, acetaldehyde, or propylene glycol, and thus has received attention as an alternative chemical material of the next generation in chemical industry.

Currently, lactate is produced by an industrially petrochemical synthesis process and a biotechnological fermentation process. The petrochemical synthesis process is performed by oxidizing ethylene derived from crude oil, preparing lactonitrile through addition of hydrogen cyanide after acetaldehyde, purifying by distillation, and hydrolyzing by using chloric acid or phosphoric acid. The biotechnological fermentation process is used to manufacture lactate from a reproducible carbon hydrate, such as, starch, sucrose, maltose, glucose, fructose, or xylose, as a substrate.

Therefore, a strain for efficiently producing lactate and a lactate production method using the strain are needed.

SUMMARY

Provided is a genetically engineered yeast cell capable of producing lactate, wherein the genetically engineered yeast cell has increased triose-phosphate isomerase (TPI) activity as compared to a yeast cell of the same species that is not genetically engineered.

Also provided is a method of producing the genetically engineered yeast cell by increasing the TPI activity of a yeast cell.

Further provided is a method of producing lactate by culturing the genetically engineered yeast cell in an appropriate medium and collecting the lactate from the culture.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
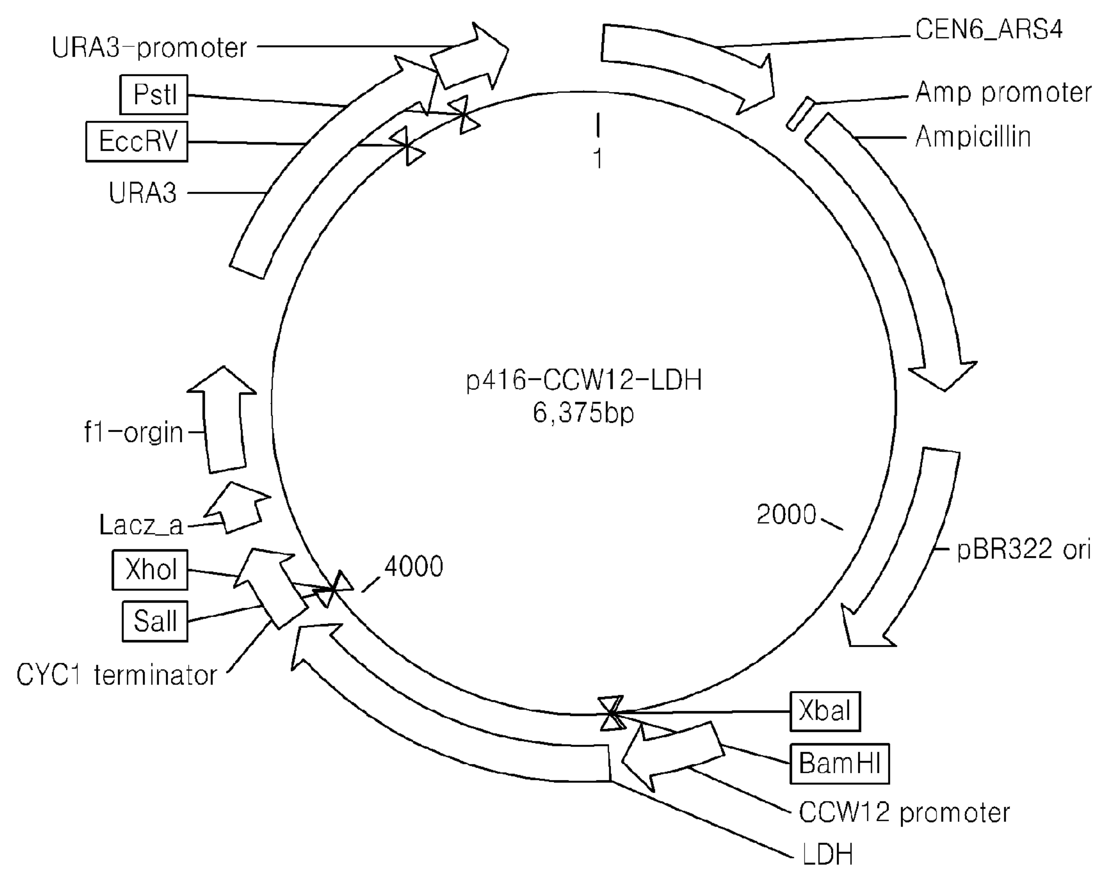
FIG. 1 is a schematic illustrating a p416-CCW12p-LDH vector.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items.

As used herein, the term "lactate" denotes a lactic acid or a salt thereof.

As used herein, the term "genetically engineered" or "genetically modified" denotes a subject (e.g., cell) having an genetic composition (genotype) that is different from a naturally occurring (wild-type) cell of the same type, the genetic composition having been altered by genetic engineering techniques. The term "genetically engineered" may include "recombinant". Recombination may include introducing exogenous nucleic acid with or without using a vehicle, such as a vector.

The genetically engineered yeast cell may be a recombinant yeast, which may include at least one recombinant nucleic acid or a recombinant protein. The recombinant yeast may include an expression vector or a cloning vector or may be genetically engineered to integrate a cloned nucleic acid sequence into the endogenous genome of the host cell. The genetic engineering includes gene modification, and the gene modification may be related to transcription, translation, and post-translation modification generating change in an enzyme's activity and/or selectivity under a selected and/or confirmed culture condition, and/or providing additional polynucleotides to increase the copy number and/or to introduce a recombinant of an enzyme in relation of lactate production.

As used herein, the terms "activity increase", "enzyme activity increase", "increased activity", or "increased enzyme activity" denote that a cell or an isolated polypeptide or enzyme has an increased activity level compared to an activity level of a comparable cell of the same type or the original, unmodified enzyme or polypeptide. The activity may be increased by any amount. For instance, an enzyme conversion activity from a substrate to a product with respect to a corresponding enzyme may be at least about 5%, at least about 10%, at least about 15%, at least about 20%, at least about 30%, at least about 50%, at least about 60%, at least about 70%, or at least about 100% increased compared to the same biochemical conversion activity of an originally uncontrolled enzyme. A cell having an increased activity of an enzyme may be confirmed by using any method commonly known in the art such as high pressure liquid chromatography (HPLC).

As used herein, "inactivated" or "reduced" activity of a cell, an enzyme or a polypeptide, denotes a cell, an enzyme, or a polypeptide having an activity level that is lower than an activity level measured in a parent yeast cell having the original, unmodified enzyme or polypeptide. This includes a cell, an enzyme or a polypeptide having no activity. The activity may be reduced by any amount. For instance, an enzyme's conversion activity of a substrate to a product with respect to a corresponding enzyme may be reduced by about 20% or more, about 30% or more, about 40% or more, about 50% or more, about 55% or more, about 60% or more, about 70% or more, about 75% or more, about 80% or more, about 85% or more, about 90% or more, about 95% or more, or about 100% in comparison to the conversion activity of an enzyme that has not undergone a subject modification, e.g., a deletion or disruption mutation. The cells having reduced activity of the enzyme may be confirmed by using a commonly known method in the art. The inactivation or reduction includes the cases where a gene encoding an enzyme is not expressed or also where a gene encoding an enzyme has a lower level of expression compared to the expression level of the gene that has not undergone a subject modification, e.g., a deletion or disruption mutation, even when the enzyme is expressed or when an activity of the enzyme is removed or reduced.

An activity of the enzyme may be inactivated or reduced due to substitution, addition, or deletion of a part or a whole gene encoding the enzyme (e.g., a substitution, addition, or deletion mutation). For example, inactivation or reduction of the enzyme may be caused by homologous recombination or may be performed by transforming a vector including a part of sequence of the gene to the cell, culturing the cell so that the sequence may homogonously recombined with an endogenous gene of the cell, and then selecting cells, in which homologous recombination occurred, using a selection marker.

As used herein, the term "sequence identity" of a nucleic acid or a polypeptide refers to a degree of similarity of base groups or amino acid residues between two aligned sequences, when the two sequences are aligned to match each other as possible, at corresponding positions. The sequence identity is a value that is measured by aligning to an optimum state and comparing the two sequences at a particular comparing region, wherein a part of the sequence within the particular comparing region may be added or deleted compared to a reference sequence. A sequence identity percentage may be calculated, for example, by 1) comparing the two sequences aligned within the whole comparing region to an optimum 2) obtaining the number of matched locations by determining the number of locations represented by the same amino acids of nucleic acids in both of the sequences, 3) dividing the number of the matched locations by the total number of the locations within the comparing region (i.e., a range size), and 4) obtaining a percentage of the sequence identity by multiplying 100 to the result. The sequence identity percent may be determined by using a common sequence comparing program, for example, BLASTN or BLASTP (NCBI), CLC Main Workbench (CLC bio), MegAlign™ (DNASTAR Inc).

The term "parent cell" or "parent yeast cell" or the like refers to an original cell, for example, a non-engineered cell of the same type as an engineered yeast cell. With respect to a particular genetic modification, the "parent cell" can be a cell that lacks the particular genetic modification, but is identical in all other respects. Thus, a parent cell can be a cell used as starting material to produce a genetically engineered yeast cell having an activated or increased activity of a given protein (e.g., a protein having a sequence identity of about 95% or more to a triose-phosphate isomerase).

In confirming many different polypeptides having the same or similar function or activity or polynucleotides encoding polypeptides having the same or similar function or activity, sequence identities of several values may be used. For example, the sequence identities may include about 50% or greater, about 55% or greater, about 60% or greater, about 65% or greater, about 70% or greater, about 75% or greater, about 80% or greater, about 85% or greater, about 90% or greater, about 95% or greater, about 96% or greater, about 97% or greater, about 98% or greater, about 99% or greater, or 100%.

The genetically engineered yeast cell may have a lactate-producing capability. The yeast cell may produce lactate at a percent yield of 34% or greater, for example, from 34 to 45%, 34 to 41%, from 35 to 41%, from 36 to 41%, from 37 to 41%, from 38 to 41%, from 38.5 to 40.5%, or from 39 to 40.5% with respect to glucose, i.e. the amount of lactate produced by the yeast cell divided by the glucose consumed by the yeast cell multiplied by 100.

Also, the lactate productivity of the genetically engineered cell may have a percent yield which is 9% or more, for example, from 9 to 25%, from 10 to 25%, from 11 to 25%, from 12 to 25%, from 13 to 25%, from 14 to 25%, from 15 to 25%, from 16 to 25%, from 17 to 25%, from 18 to 25%, from 19 to 25%, from 15 to 20%, from 16 to 20%, from 17 to 20%, from 18 to 20%, or from 19 to 20% increased compared to the lactate productivity of a cell that is not genetically engineered. The genetic engineering may increase an activity of polypeptide of triose-phosphate isomerase (TPI).

As used herein, the cell that is not genetically engineered includes a mother cell or a wild-type cell of the same species from which the yeast cell with an increased activity of TPI is derived.

As used herein, the term "triose-phosphate isomerase (TPI)" denotes an enzyme that catalyzes reversible conversion of dihydroxyacetone phosphate (DHAP) and glyceraldehyde-3-phosphate (GA3P). The TPI may be a polypeptide derived from EC 5.3.1.1.

In regard to the genetically engineered yeast cell with an increased TPI activity compared to that of a parent yeast cell, the TPI activity may be increased due to an increase in a copy number of an endogenous gene encoding TPI, or due to the introduction of an exogenous TPI gene, for instance, a TPI gene having increased activity compared to an endogenous TPI gene. The increase in copy number of the gene may be caused by introduction of exogenous TPI gene or genes, or by amplification of the endogenous gene encoding TPI. The gene encoding TPI may include an expression-regulation sequence of the gene.

The gene encoding TPI may be a heterologous gene. The term "heterologous gene" or "heterologous polynucleotide" indicates a nucleic acid or polypeptide that is not naturally found in a given host cell. The gene encoding TPI may be also a homologous gene. The homologous gene may refer to a gene from the same source as that of the recipient cell (e.g., *Saccharomyces* genus).

The term "heterologous" is understood as including the meaning of the term "exogenous", and the term "exogenous" is commonly used in the art. The heterologous gene may refer to a gene from a source different than that of the recipient cell. The nucleic acid sequence encoding an enzyme is heterologous regardless of whether the heterologous nucleic acid sequence is integrated into the genome or not. In some embodiments, the increase in TPI activity may be caused by introduction of the heterologous gene encoding TPI.

Also, the increase in TPI activity may be caused by modification of the expression-regulation sequence of the gene. The regulation sequence may be a gene encoding a motif that may affect the gene expression. The gene expression may include both transcription and translation and may be understood as including protein production. Examples of the motif that may affect the gene expression may include a secondary-structure stabilization motif, a region having increased self-homology, a region having increased homology with respect to a natural gene, an RNA destabilization motif, a splice-activation motif, a polyadenylation motif, an adenine-rich sequence, and an endonuclease recognizing site.

The regulation sequence may be an appropriate promoter sequence, which is a nucleotide sequence that is recognized by a host cell for expression of the gene encoding TPI. The promoter sequence may include a transcription regulation sequence mediating expression of polypeptide. The promoter may be any nucleotide sequence that shows transcription activity in the host cell of choice including mutant, truncated, and hybrid promoters, and may be obtained from a gene encoding extracellular or intracellular polypeptides either homologous or heterologous to the host cell.

The regulation sequence may also include an appropriate transcription terminator sequence which is recognized by a host cell to terminate the transcription. The terminator sequence may be operably linked to a 3' terminal of a nucleotide sequence encoding a polypeptide. The terminator sequence may be an arbitrary terminator functioning in a yeast cell. Also, a regulation sequence that regulates expression of a polypeptide in regard of growth of the host cell may be added. An example of a control system may be a system that turns on or off expression of the gene in response to a chemical or physical stimulus caused by presence of a control compound (i.e. an inducible expression system).

Also, the increase in TPI activity may be due to modification caused by mutation of TPI polypeptide.

The TPI-encoding gene may be derived from bacteria, yeast, fungus, or mammals. The yeast may include a *Saccharomyces* genus. The mammals may include a rabbit. The rabbit may be European rabbit (*Oryctolagus cuniculus*) or cottontail rabbit (genus *Sylvilagus*). The TPI may be derived from *Saccharomyces cerevisiae, Trypanosoma brucei*, a rabbit, or a combination thereof. The TPI derived from *Saccharomyces cerevisiae* may be one of proteins shown in Table 1. The TPI derived from the rabbit muscle cell may be one of proteins shown in Table 3.

TABLE 1

TPI derived from *Saccharomyces cerevisiae* and its gene

| SEQ ID NO | strain | gene |
|---|---|---|
| 1 | strain ATCC 204508/S288c | TPI1 YDR050C YD9609.05C |
| | strain AWRI1631 | AWRI1631_42730 |
| | strain AWRI796 | AWRI796_0798 |
| | strain FostersB | FOSTERSB_0776 |
| | strain JAY291 | TPI1 C1Q_03637 |
| | strain Kyokai no. 7/NBRC 101557 | K7_TPI1 SYK7_012011 |
| | strain Lalvin EC1118/Prise de mousse | EC1118_1D0_2949g |
| | strain Lalvin QA23 | QA23_0786 |
| | strain RM11-1a | SCRG_00464 |
| | strain VIN 13 | VIN13_0785 |
| | strain YJM789 | TPI1 SCY_0954 |
| | *Saccharomyces kudriavzevii* VIN7 | VIN7_0778 |
| 2 | strain FostersO | FOSTERSO_0623 |
| 3 | strain Zymaflore VL3 | VL3_0789 |
| 4 | *Saccharomyces kudriavzevii* VIN7 | VIN7_6169 |

TABLE 2

TPI derived from *Trypanosoma brucei* gambiense and its gene

| SEQ ID NO | strain | Gene |
|---|---|---|
| 5 | *T. brucei brucei* (strain 927/4 GUTat10.1) | Tb11.02.3210 |
| | *T. brucei gambiense* (strain MHOM/CI/86/DAL972) | TbgDal_XI6230 |
| | *T. brucei gambiense* (strain MHOM/CI/86/DAL972) | TbgDal_IX5650 |
| 6 | *T. brucei brucei* | |
| 7 | *T. brucei brucei* (strain 927/4 GUTat10.1) | Tb09.211.1370 |

TABLE 3

TPI derived a rabbit muscle cell and its gene

| SEQ ID NO | strain | Gene |
|---|---|---|
| 8 | *Oryctolagus cuniculus* (Rabbit) | TPI1 |
| 9 | *Oryctolagus cuniculus* (Rabbit) | LOC100348316 |

The TPI may have an amino acid sequence having about 50% or more, 60% or more, 70% or more, 80% or more, 90% or more, 95% or more, 96% or more, 97% or more, 98% or more, 99% or more, or 100% of sequence identity with one amino acid sequence selected from among SEQ ID NO: 1 to 9. The gene encoding TPI may be one of genes shown in Tables 1 to 3. The gene encoding TPI may have one polynucleotide sequence selected from among SEQ ID NOS: 10 to 13.

Also, the yeast cell may be a mutated yeast cell for producing lactate in addition to a wild yeast cell. The mutated yeast cell may include other mutations, such as a mutation that renders the yeast cell resistant to an acid such as lactic acid, or lactate. Also, the mutated yeast cell may further include a natural LDH gene.

The yeast cell may be ascomycota. The ascomycota may be saccharomycetaceae. The saccharomycetaceae may be *Saccharomyces* genus, *Kluyveromyces* genus, *Candida* genus, *Pichia* genus, *Issatchenkia* genus, *Debaryomyces* genus, *Zygosaccharomyces* genus, or *Saccharomycopsis* genus. The *Saccharomyces* genus may be, for example, *S. cerevisiae, S. bayanus, S. boulardii, S. bulderi, S. cariocanus, S. cariocus, S. chevalieri, S. dairenensis, S. ellipsoideus, S. eubayanus, S. exiguus, S. florentinus, S. kluyveri, S. martiniae, S. monacensis, S. norbensis, S. paradoxus, S. pastorianus, S. spencerorum, S. turicensis, S. unisporus, S. uvarum*, or *S. zonatus*. The *Kluyveromyces* genus may be *Kluyveromyces thermotolerans*. The *Candida* genus may be *Candida glabrata*. The *Zygosaccharomyces* genus may be *Zygosaccharomyces bailli* or *Zygosaccharomyces rouxii*.

The genetically engineered yeast cell may also be modified such that the activity of a polypeptide converting pyruvate to acetaldehyde, a polypeptide converting lactate to pyruvate, a polypeptide converting dihydroxyacetone phosphate (DHAP) to glycerol-3-phosphate, or a combination thereof may be inactivated or decreased. Activity of a polypeptide may be inactivated or decreased due to deletion or disruption of a gene encoding the polypeptide. As used herein, the "deletion" or "disruption" of the gene includes mutation or deletion of the gene or a regulatory region of the gene (e.g., operator, promoter or terminator regions of the gene), or a part thereof, sufficient to disrupt or delete gene function or the expression of a functional gene product. Mutations include substitutions, additions, and deletions of one or more bases in the gene or its regulator regions. As a result, the gene is not expressed or has a reduced amount of expression, or the activity of the encoded protein or enzyme is reduced or eliminated. The deletion or disruption of the gene may be accomplished by any suitable genetic engineering technique, such as homologous recombination, mutation induction, or directed molecular evolution. When a cell includes a plurality of copies of the same gene or at least two different polypeptide paralogs, at least one gene may be deleted or disrupted.

In the yeast cell, an activity of a polypeptide converting pyruvate to acetaldehyde may be inactivated or decreased. The polypeptide converting pyruvate to acetaldehyde may be an enzyme which is classified to EC 4.1.1.1. The enzyme may be a pyruvate decarboxylase. For example, the enzyme may be PDC1, PDC2, PDC3, PDC4, PDC5 or PDC6. The polypeptide converting pyruvate to acetaldehyde may have an amino acid sequence having about 50% or more, 60% or more, 70% or more, 80% or more, 90% or more, 95% or more, 96% or more, 97% or more, 98% or more, 99% or more, or 100% of sequence identity with an amino acid sequence of SEQ ID NO: 14. The gene encoding the polypeptide converting pyruvate to acetaldehyde may have a nucleotide sequence of SEQ ID NO: 15. The gene may be a pdc gene encoding a pyruvate decarboxylase (PDC).

In the yeast cell, an activity of the polypeptide converting pyruvate to lactate may be inactivated or decreased. The polypeptide converting pyruvate to lactate may be a cytochrome c-dependent enzyme. The polypeptide converting pyruvate to lactate may be a lactate cytochrome c-oxidoreductase. The lactate cytochrome c-oxidoreductase may be an enzyme that is classified to EC 1.1.2.4 working on D-lactate or an enzyme that is classified to EC 1.1.2.3 working on L-lactate. The enzyme may be Cyb2. The polypeptide converting lactate to pyruvate may have about 50% or more, 60% or more, 70% or more, 80% or more, 90% or more, 95% or more, 96% or more, 97% or more, 98% or more, 99% or more, or 100% of sequence identity with an amino acid sequence of SEQ ID NO: 16. The gene encoding the polypeptide converting lactate to pyruvate may have a nucleotide sequence of SEQ ID NO: 17.

In the yeast cell, an activity of the polypeptide converting DHAP to glycerol-3-phosphate may be inactivated or decreased. The polypeptide converting DHAP to glycerol-3-phosphate may be a cytosolic glycerol-3-phosphate dehydrogenase. The enzyme may catalyze reduction of DHAP to glycerol-3-phosphate by using oxidation of NADH to $NAD^+$. The enzyme may belong to EC 1.1.1.8 and may be GPD1 or GPD2. The GPD1 may have an amino acid sequence having about 50% or more, 60% or more, 70% or more, 80% or more, 90% or more, 95% or more, 96% or more, 97% or more, 98% or more, 99% or more, or 100% or sequence identity with an amino acid sequence of SEQ ID NO: 18. The gene encoding GPD1 may have a nucleotide sequence of SEQ ID NO: 19.

In the yeast cell, an activity of converting pyruvate to lactate may be increased. The activity of converting pyruvate to lactate may be increased sufficiently enough to produce lactate.

The increase in activity of converting pyruvate to lactate may be caused by introduction of a polypeptide (or nucleic acid encoding the polypeptide) that converts pyruvate to lactate, or an increase in the expression of an existing nucleic acid encoding such a polypeptide. The increase in the expression may be caused by an increase in the copy number of a gene or by mutation of a control region of a gene. The increase in the copy number of a gene may be caused by amplification of an endogenous gene or by introduction of an exogenous gene. The mutation of the control region of the gene may be caused by mutation of a control region of an endogenous gene. The source of the exogenous gene may be a homogenous or heterogenous. The homogenous gene may be composed of elements that are all of the same kind as those of a recipient cell, whereas the heterogenous gene may be composed of elements that are of a different kind from those of a recipient cell.

The polypeptide converting pyruvate to lactate may be a lactate dehydrogenase. The lactate dehydrogenase may catalyze conversion of pyruvate to lactate. The lactate dehydrogenase may be an NAD(P)-dependent enzyme which may be L-lactate dehydrogenase or D-lactate dehydrogenase. The NAD(P)-dependent enzyme may be an enzyme that is classified to EC 1.1.1.27 which works on L-lactate or EC 1.1.1.28 which works on D-lactate.

The yeast cell may include a plurality of genes encoding a lactate dehydrogenase. The polynucleotide encoding lactate dehydrogenase may be derived from bacteria, yeasts, and fungus, mammals, or reptiles. The polynucleotide may be a polynucleotide that encodes at least one LDH selected from *Pelodiscus sinensis japonicus, Ornithorhynchus anatinus, Tursiops truncatus, Rattus norvegicus*, and *Xenopus laevis* LDH proteins. A lactate dehydrogenase derived from *Pelodiscus sinensis japonicas*, a lactate dehydrogenase derived from *Ornithorhynchus anatinus*, a lactate dehydrogenase derived from *Tursiops truncatus*, a lactate dehydrogenase derived from *Rattus norvegicus*, and a lactate dehydrogenase derived from *Xenopus laevis* may be, each respectively, have amino acid sequences having about 50% or more, 60% or more, 70% or more, 80% or more, 90% or more, 95% or more, 96% or more, 97% or more, 98% or more, 99% or more, or 100% of sequence identity with amino acid sequences of SEQ ID NO: 20, 21, 22, and 23. A gene that encodes the lactate dehydrogenase may have a nucleotide sequence of SEQ ID NO: 24.

The polynucleotide encoding LDH may be expressed from a vector including LDH derived from bacteria, yeast, fungus, mammals, or reptiles. The vector may include a replication origin, a promoter, a polynucleotide encoding a lactate dehydrogenase, and a terminator. The replication origin may include a yeast autonomous replication sequence (ARS). The yeast ARS may be stabilized by a yeast centrometric sequence (CEN). The promoter may be selected from the group consisting of a CYC promoter, a TEF promoter, a GPD promoter, and an ADH promoter. The CYC promoter, TEF promoter, GPD promoter, and ADH promoter may have, each respectively, nucleotide sequences of SEQ ID NO: 26, 27, 28, and 29. The terminator may be selected from the group consisting of phosphoglycerate kinase 1 (PGK1), cytochrome c transcription (CYC1), and GAL1. The CYC1 terminator may have a nucleotide sequence of SEQ ID NO: 30. The vector may further include a selection marker.

The polynucleotide encoding LDH may be included in a genome of a yeast cell. When the polynucleotide encoding LDH functions to produce active protein in a cell, the polynucleotide is deemed as "functional" in a cell. A yeast cell including the polynucleotide encoding the L-lactate dehydrogenase or the D-lactate dehydrogenase may produce a L-lactate enantiomer, a D-lactate enantiomer, or a salt thereof.

The yeast cell may include a polynucleotide encoding one LDH or a polynucleotide encoding multiple LDHs to 1 to 10 copies. The polynucleotide encoding the multiple LDHs may be a polynucleotide encoding, for example, 1 to 8, 1 to 7, 1 to 6, 1 to 5, 1 to 4, or 1 to 3 copies of LDHs. When the yeast cell includes the polynucleotide encoding multiple LDHs, the polynucleotide may include copies of the same polynucleotide or copies of polynucleotides encoding at least two different LDHs. The multiple copies of the polynucleotide encoding exogenous LDHs may be included in the same gene locus or multiple gene loci in a genome of a host cell. In this sense, a single "gene" may contain multiple copies of a polynucleotide encoding the same LDH or multiple copies of polynucleotides encoding at least two different LDHs.

Moreover, the yeast cell may be *Saccharomyces cerevisiae*, in which activities of a polypeptide encoding TPI and a polypeptide converting pyruvate to lactate are increased and activities of a polypeptide converting pyruvate to acetaldehyde, a polypeptide converting lactate to pyruvate, a polypeptide converting DHAP to glycerol-3-phosphate, and a combination thereof are inactivated or reduced. An expression vector including the polynucleotide encoding TPI for constructing a genetically engineered yeast cell capable of producing lactate, wherein the yeast cell is modified to have an increased copy number of genes encoding TPI or the increased expression compared to a cell that is not genetically engineered.

The polynucleotide may be operably linked to a regulation sequence appropriate for expressing the polynucleotide in an appropriate host. The regulation sequence may include a promoter, a terminator, or an enhancer. Also, the promoter may be operably linked with a sequence encoding a gene. As used here, the term "operably linked" denotes a functional connection between a nucleic acid expression-regulation sequence and another nucleotide sequence. In this regard, the regulation sequence may control transcription and/or translation of a nucleotide sequence encoding the gene.

The expression vector may be a yeast expression vector, a bacteriophage vector, or a cosmid vector. The yeast expression vector may be, for example, a vector for expression in *Saccharomyces cerevisiae*, and examples of the yeast expression vector may include pYepSec1, 2i, pAG-1, Yep6, Yep13, PEMBLYe23, pMFa, pJRY88, pYES2, and *Saccharomyces cerevisiae/Escherichia coli* shuttle vector, and pRS400-series vectors, such as a pRS416 vector.

In order to serve as an expression vector, the vector may include a replication origin, a promoter, a multiple cloning site (MCS), and a selection marker. The replication origin serves to allow a plasmid to have a replicating function independent from chromosomal replication in a host cell, the promoter works on the transcription process of an exogenous gene being inserted, the MCS allows the exogenous gene to be inserted through various restriction enzyme sites, and the selection marker serves to confirm whether the vector is properly introduced to the host cell. The selection marker includes an antibiotic-resistive gene, for example, a gene that is resistive to ampicillin, gentamicin, carbenicillin, chloramphenicol, streptomycin, kanamycin, geneticin, neomycin, or tetracycline. Also, the selection marker may include an auxotrophic gene and may include, for example, a gene providing auxotrophy to one selected from uracil, tryptophan, leucine, and histidine.

Examples of the promoter appropriate for directing transcription of a nucleic acid in a yeast host cell including *Saccharomyces* genus include a PGK promoter, a GPD promoter, a PDC1 promoter, and a TEF1 promoter.

According to an aspect of the present disclosure, a genetically engineered yeast cell capable of producing lactate is provided, wherein the cell has an increased activity of triose-phosphate isomerase (TPI) compared to that of a parent cell.

According to another aspect of the present disclosure, a genetically engineered yeast cell capable of producing lactate is provided, wherein the yeast cell is modified to have an increased copy number of a gene encoding TPI or an increased expression of the gene compared to that of a parent cell.

According to another aspect of the present disclosure, a method of preparing a genetically engineered yeast cell capable of producing lactate includes introducing a polynucleotide encoding TPI to yeast is provided.

In the method, the genetically engineered yeast cell may be modified to have an increased copy number of a gene encoding TPI or the increased expression compared to a cell that is not genetically engineered. The increase in the copy number may be caused by introduction or amplification of the gene.

Also, the TPI may catalyze conversion of DHAP to glyceraldehyde-3-phosphate (GA3P).

According to another aspect of the present disclosure, a method of preparing the genetically engineered yeast cell is provided, the method including introducing a polynucleotide encoding TPI into a yeast cell. The descriptions of TPI and the genetically engineered yeast cell are as defined in the specification.

The method may include inactivating or decreasing activities of a pyruvate decarboxylase gene, a lactate cytochrome-c oxydoreductase, a glycerol-3-phosphate dehydrogenase gene, and a combination thereof. The descriptions of the pyruvate decarboxylase gene, lactate cytochrome-c oxydoreductase, and glycerol-3-phosphate dehydrogenase gene are as defined in the specification.

The method may also include introducing a polynucleotide encoding a lactate dehydrogenase into the yeast cell. The description of the lactate dehydrogenase is as defined above in the specification.

According to another aspect of the present disclosure, a method of preparing lactate using the genetically engineered yeast cell is provided. The method may include culturing the genetically engineered yeast cell in an appropriate medium; and collecting lactate from the culture. The description of the genetically engineered yeast cell is as defined above in the specification.

The culturing may be performed in a carbon source, for example, a medium containing glucose. The medium used in the culturing of a yeast cell may be a common medium suitable for growth of a host cell such as a minimal or composite medium containing appropriate supplements. A suitable medium may be purchased from commercial suppliers or may be prepared according to a known preparation method.

The medium used in the culturing may be a medium that satisfies particular conditions for growing a yeast cell. The medium may be one selected from the group consisting of a carbon source, a nitrogen source, a salt, trace elements, and a combination thereof.

The culturing condition for obtaining lactate from the genetically engineered yeast cell may be appropriately controlled. The culturing may be performed in an aerobic or anaerobic condition. For example, the yeast cell is cultured under an aerobic condition for its proliferation, and then, the yeast cell is cultured under an anaerobic condition to produce lactate. The anaerobic condition may include a dissolved oxygen (DO) concentration of 0% to 10%, for example, 0% to 8%, 0% to 6%, 0% to 4%, or 0% to 2%.

As used herein, the term "culture condition" denotes a condition for culturing a yeast cell. The culture condition may be, for example, a carbon source, nitrogen source, or oxygen condition for the yeast cell. The carbon source that is used by the yeast cell includes monosaccharides, disaccharides, or polysaccharides. In particular, glucose, fructose, mannose, or galactose may be used. The nitrogen source that is used by the yeast cell may be an organic nitrogen compound or an inorganic nitrogen compound. In particular, amino acid, amide, amine, nitrate, or ammonium salt may be used. An oxygen condition for culturing yeast cell may be an aerobic condition of a normal oxygen partial pressure, a low-oxygen condition including 0.1% to 10% of oxygen in the atmosphere, or an anaerobic condition including no oxygen. A metabolic pathway may be modified in accordance with a carbon source or nitrogen that may be actually used by a yeast cell.

Isolation of lactate from the culture may be performed by an isolation method commonly known in the art. The isolation method may be centrifugation, filtration, ion-exchange chromatography, or crystallization. For example, a supernatant obtained by centrifuging the culture at a low speed and removing a biomass may be separated through ion-exchange chromatography.

The method may further include polymerizing the lactate to form a polylactate polymer.

The present disclosure will be described in further detail with reference to the following examples. These examples are for illustrative purposes only and are not intended to limit the scope of the present invention.

Example 1

Preparation of Strain for Highly-Efficient Production of Lactate and Preparation of Expression Vector In order to block a production pathway of ethanol and glycerol as main byproducts by using *Saccharomyces cerevisiae* CEN.PK2-1D (*S. cerevisiae* CEN.PK2-1D (MATα ura3-52; trp1-289; leu2-3,112; his3Δ 1; MAL2-8$^c$; SUC2) EUROSCARF accession number: 30000B) as a lactate production strain, a pyruvate decarboxylase (pdc1) gene, which is a main enzyme of alcohol fermentation, a NAD-dependent glycerol-3-phosphate dehydrogenase (gpd1) gene, which is a main enzyme of glycerol biosynthesis, and a L-lactate cytochrome-c oxidoreductase2 (cyb2) gene, which is a lactate lyase, were deleted from the strain to be used as a strain for producing lactate. Also, in order to produce lactate, a lactate dehydrogenase (ldh) gene of SEQ ID NO: 24 was inserted to each of the removal locations while simultaneously removing the three genes, and thus 3 copies of lactate dehydrogenases were inserted to the strain.

The removal of each of the genes and the simultaneous insertion of the lactate dehydrogenase genes were performed by homologous recombination at an upstream part and a downstream part of target locus of an open reading frame of each of the genes to be removed or a region including a promoter and a terminator.

(1.1) Preparation of a L-LDH Overexpression Vector and a Gene Exchange Vector for Inactivating pdc1, gpd1, and Cyb2 Genes (1.1.1) Preparation of a L-LDH Overexpression Vector A CCW12 promoter PCR fragment obtained by performing Polymerase Chain Reaction (PCR) with a genomic DNA of *Saccharomyces cerevisiae* CEN.PK2-1D as a template and using primers of SEQ ID NO: 31 and SEQ ID NO: 32 was digested with SacI and XbaI, and the resultant was inserted into p416-GPD vector (ATCC 87360™) digested with SacI and XbaI, producing p416-CCW12p vector.

Then, L-ldh gene (SEQ ID NO: 24) was amplified from *Pelodiscus sinensis japonicus* genomic DNA by PCR using primers of SEQ ID NO: 33 and SEQ ID NO: 34. The resulting L-ldh PCR fragment and p416-CCW12p obtained therefrom were digested with BamHI and SalI, and ligated, producing p416-CCW12p-LDH, which is a L-ldh expression vector.

The L-ldh expression vector has also a yeast autonomous replication sequence (ARS)/a yeast centrometric sequence (CEN) of SEQ ID NO: 25, a CYC promoter of SEQ ID NO: 26, a GPD promoter of SEQ ID NO: 27, and a CYC1 terminator of SEQ ID NO: 28. The L-ldh expression vector included a polynucleotide encoding L-ldh derived from *Pelodiscus sinensis japonicus* of SEQ ID NO: 24.

FIG. 1 is a view illustrating a p416-CCW12p-LDH vector. As shown in FIG. 1, the LDH derived from *Pelodiscus sinensis japonicus* was introduced into the vector.

(1.1.2) Preparation of a Gene Exchange Vector

Figure 2:
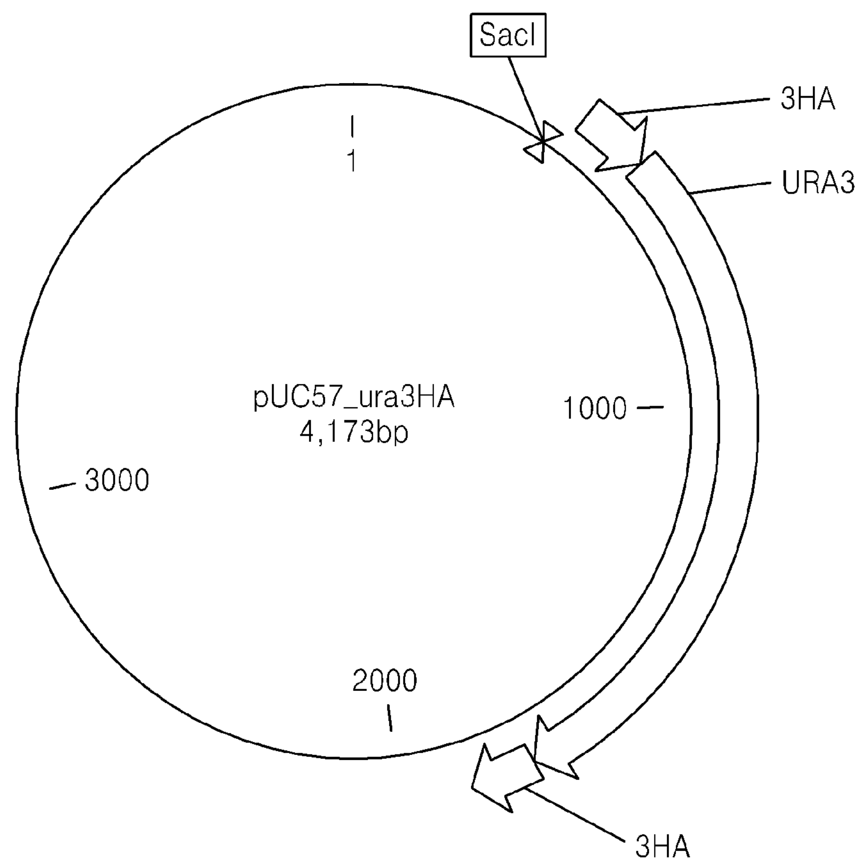
FIG. 2 is a schematic illustrating a pUC57-ura3HA (Genetics 116: 541-545, August, 1987) vector.
Figure 3:
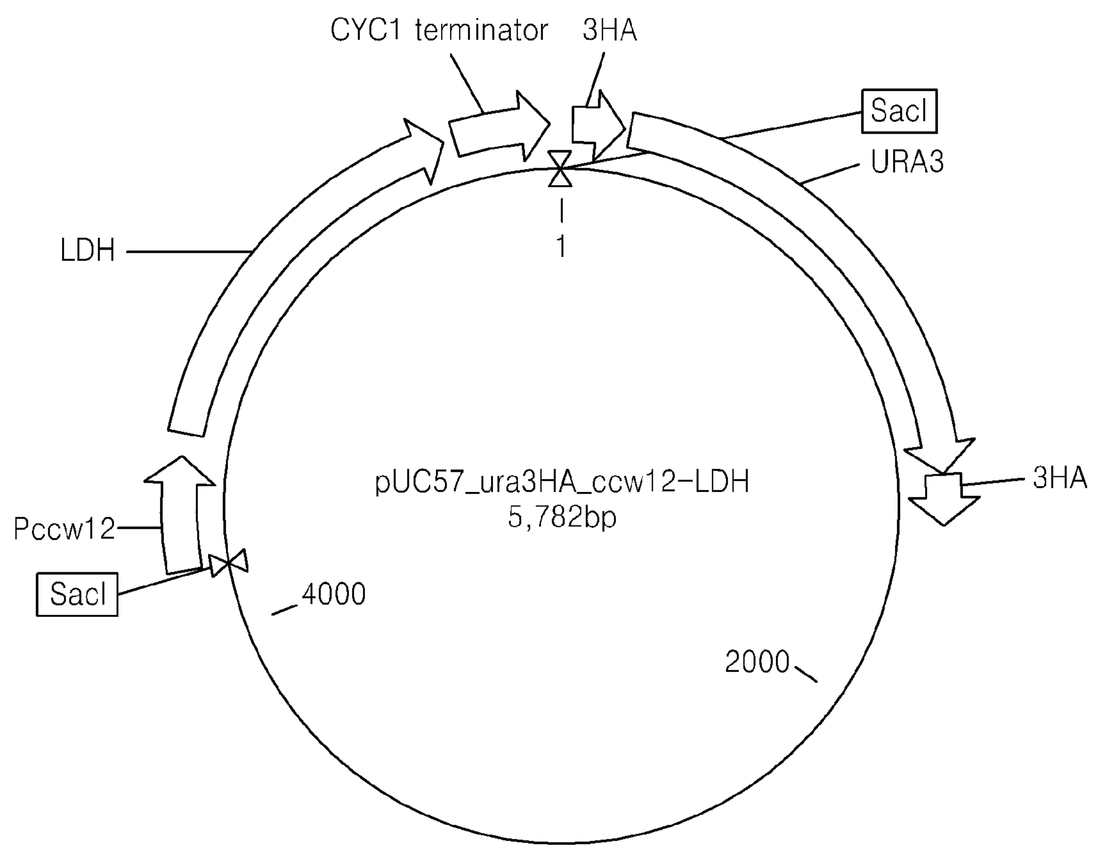
FIG. 3 is a schematic illustrating a pUC57-ura3HA-ccw12p-LDH vector.

PDC1, CYB2, and GPD1 genes were deleted by using a homologous recombination method, and at the same time, a gene exchange vector for introducing a L-LDH gene was prepared in the same manner described below. FIG. 2 illustrates a pUC57-ura3HA (Genetics 116: 541-545, August, 1987) vector. FIG. 3 illustrates a pUC57-ura3HA-CCW12p-LDH vector.

PCR was performed using the prepared p416-CCW12p-LDH as a template with primers of SEQ ID NOS: 35 and 36. The resulting PCR fragment and the prepared pUC57- ura3HA vector were digested with SacI and ligated, producing pUC57-ura3HA-CCW12p-LDH.

PCR was performed using the produced pUC57-ura3HA-CCW12p-LDH as a template with primers of SEQ ID NOS: 37 and 38, producing a PDC1 gene deletion cassette.

PCR was performed using the produced pUC57-ura3HA-CCW12p-LDH as a template with primers of SEQ ID NOS: 39 and 40, producing a CYB2 gene deletion cassette.

PCR was performed using the produced pUC57-ura3HA-CCW12p-LDH as a template with primers of SEQ ID NOS: 41 and 42, producing a GPD1 gene deletion cassette.

(1.2) Inactivation of pdc1, gpd1, and cyb2 Genes

A mutant strain of *Saccharomyces cerevisiae* CEN.PK2-1D, in which pdc1 is deleted, was produced in the same manner as follows. *Saccharomyces cerevisiae* CEN.PK2-1D was plated onto a YPD agar plate (including 10 g of yeast extract, 20 g of peptone, and 20 g of glucose) and incubated for 24 hours at 30° C., and then, a colony obtained therefrom was inoculated in about 10 ml of a YPD liquid medium and cultured for about 18 hours at about 30° C. The sufficiently grown culture solution was inoculated in about 50 ml of a YPD liquid medium contained in a 250 ml-flask at a concentration of 1% (v/v) and cultured in an incubator at a rate of about 230 rpm and at 30° C. After about 4 to 5 hours, when the optical density measured at 600 nanometers ($OD_{600}$) reached about 0.5, the culture was centrifuged at a rate of about 4,500 rpm for about 10 minutes to harvest cells, and the cells were resuspended in a lithium acetate solution at a concentration of about 100 mM. Then, the cells were harvested by performing centrifugation at a rate of about 4,500 rpm for about 10 minutes, resuspended in a lithium acetate solution at a concentration of about 1 M including about 15% of glycerol, and then divided into 100 ul aliquots each.

In order to delete a pdc1 gene, the above yeast component cell and the PDC1 deletion cassette produced in Example 1.1.2 were mixed with 50% of polyethylene glycol and a single stranded carrier DNA and reacted in a water tub for about 1 hour at 42° C., and then, the culture solution was spread on a uracil-free minimal agar plate (including YSD, 6.7 g/L of yeast nitrogen base without amino acids, and 1.4 g/L of amino acid dropout mix (-ura)) and grown for about 24 hours or more at 30° C. Ten colonies (mutant strains) grown on the plate were selected, patched onto the fresh uracil-free minimal agar plate, and at the same time, inoculated into a liquid medium including the same components contained in the uracil-free minimal agar plate to isolate the genomic DNA from the above mutant strains by using a commonly used kit (Gentra Puregene Cell kit, Qiagen, USA). In order to confirm deletion of pdc1 gene, PCR was performed using the isolated genomic DNA of the mutant strain as a template with primers of SEQ ID NOS: 43 and 44, and then, electrophoresis was performed on the obtained PCR product to confirm pdc1 deletion. As a result, *Saccharomyces cerevisiae* CEN.PK2-1D (Δ pdc1::ldh+ura3) was obtained.

Also, for additional gene deletion using the gene exchange vector, a selection marker URA3 gene, which was introduced for the preparation of a CEN.PK2-1D (Δ pdc1::ldh+ura3) strain, was removed from the strain. *Saccharomyces cerevisiae* CEN.PK2-1D (Δ pdc1::ldh+ura3) was inoculated in about 10 ml of a YPD liquid medium, cultured for about 18 hours at 30° C., and spread on a 5-FOA plate (including YSD, 6.7 g/L of yeast nitrogen base without amino acids, 1.4 g/L of an amino acid dropout mix, and 1 μg/L of 5-fluoroorotic acid), and cultured for about 24 hours or more at 30° C. Ten colonies (a URA3 pop-out strain) grown on the 5-FOA plate were selected, patched onto the fresh 5-FOA plate, and, at the same time, cultured in a YPD liquid medium to isolate genomic DNA from the selected strain by using a commonly used kit (Gentra Puregene Cell kit, Qiagen, USA). In order to confirm deletion of URA3 gene by using the isolated genomic DNA of the URA3 pop-out strain as a template, PCR was performed using primers of SEQ ID NOS: 43 and 44, and then electrophoresis was performed on the obtained PCR product to confirm deletion of URA3 gene. As a result, *Saccharomyces cerevisiae* CEN.PK2-1D (Δ pdc1::ldh) was obtained.

Deletion of the cyb2 gene in *Saccharomyces cerevisiae* CEN.PK2-1D (Δpdc1::ldh) was prepared in the same manner, as follows. *Saccharomyces cerevisiae* CEN.PK2-1D (Δpdc1::ldh) was plated onto a YPD agar plate (including 10 g of yeast extract, 20 g of peptone, and 20 g of glucose) and incubated for 24 hours at 30° C., and then, a colony obtained therefrom was inoculated in about 10 ml of a YPD liquid medium and cultured for about 18 hours at 30° C. The sufficiently grown culture solution was inoculated in about 50 ml of a YPD liquid medium contained in a 250 ml-flask at a concentration of 1% (v/v) and cultured in an incubator at a rate of about 230 rpm and at 30° C. After about 4 to 5 hours, when the $OD_{600}$ reached about 0.5, the culture was centrifuged at a rate of about 4,500 rpm for about 10 minutes to harvest cells, and the cells were resuspended in a lithium acetate solution at a concentration of about 100 mM. Then, the cells were harvested by performing centrifugation at a rate of about 4,500 rpm for about 10 minutes, resuspended in a lithium acetate solution at a concentration of about 1 M including about 15% of glycerol, and then divided into 100 ul aliquots each.

In order to delete a cyb2 gene, a cyb2 deletion cassette, which is prepared in Examples 1 and 2 in the same manner as the pdc1 deletion cassette was prepared in Example 1.1.2, and the above pdc1-deleted competent cell were mixed with 50% of polyethylene glycol and a single stranded carrier DNA and reacted in a water tub for about 1 hour at 42° C., and then, the culture solution was spread on a uracil-free minimal agar plate (including YSD, 6.7 g/L of yeast nitrogen base without amino acids, and 1.4 g/L of amino acid dropout mix (-ura)) and grown for about 24 hours or more at 30° C. Ten colonies (mutant strains) grown on the plate were selected, patched onto the fresh uracil-free minimal agar plate, and at the same time, inoculated into a liquid medium including the same components contained in the uracil-free minimal agar plate to isolate the genomic DNA from the above mutant strains by using a commonly used kit (Gentra Puregene Cell kit, Qiagen, USA). In order to confirm deletion of cyb2 gene, PCR was performed using the isolated genomic DNA of the mutant stain as a template with using primers of SEQ ID NOS: 45 and 46, and then, electrophoresis was performed on the obtained PCR product to confirm cyb2 deletion. As a result, *Saccharomyces cerevisiae* CEN.PK2-1D (Δ pdc1::ldh Δ cyb2::ldh+ura3) was obtained.

Also, for additional gene deletion using the gene exchange vector, a URA3 gene as a selection marker of the cyb2 deletion cassette was removed by using the URA3 pop-out method as described above. *Saccharomyces cerevisiae* CEN.PK2-1D (Δpdc1::ldh Δcyb2::ldh+ura3) was inoculated in about 10 ml of a YPD liquid medium, cultured for about 18 hours at 30° C., and spread on a 5-FOA plate (including YSD, 6.7 g/L of yeast nitrogen base without amino acids, 1.4 g/L of an amino acid dropout mix, and 1 μg/L of 5-fluoroorotic acid), and cultured for about 24 hours or more at 30° C. Ten colonies (a URA3 pop-out strain)

grown on the 5-FOA plate were selected, patched onto the fresh 5-FOA plate, and, at the same time, cultured in a YPD liquid medium to isolate genomic DNA from the selected strain by using a commonly used kit (Gentra Puregene Cell kit, Qiagen, USA). In order to confirm deletion of URA3 gene by using the isolated genomic DNA of the URA3 pop-out strain as a template, PCR was performed using primers of SEQ ID NOS: 45 and 46, and then electrophoresis was performed on the obtained PCR product to confirm deletion of URA3 gene. As a result, *Saccharomyces cerevisiae* CEN.PK2-1D (Δpdc1::ldh Δcyb2::ldh) was obtained.

A gpd1 deletion strain of *Saccharomyces cerevisiae* CEN.PK2-1D (Δ pdc1::ldhΔcyb2::ldh) was prepared in the same manner as follows. *Saccharomyces cerevisiae* CEN.PK2-1D (Δpdc1::ldhΔcyb2::ldh) was plated onto a YPD agar plate (including 10 g of yeast extract, 20 g of peptone, and 20 g of glucose) and cultured for about 24 hours at 30° C., and then, a colony obtained therefrom was inoculated in about 10 ml of a YPD liquid medium and cultured for about 18 hours at 30° C. The sufficiently grown culture solution was inoculated in about 50 ml of a YPD liquid medium contained in a 250 ml-flask at a concentration of 1% (v/v) and cultured in an incubator at a rate of about 230 rpm and a temperature of about 30° C. After about 4 to 5 hours, when the $OD_{600}$ reached about 0.5, the culture was centrifuged at a rate of about 4,500 rpm for about 10 minutes to obtain cells, and the cells were resuspended in a lithium acetate solution at a concentration of about 100 mM. Then, the cells were obtained by performing centrifugation at a rate of about 4,500 rpm for about 10 minutes, resuspended in a lithium acetate solution at a concentration of about 1 M including about 15% of glycerol, and then divided into 100 ul aliquots each.

In order to delete a gpd1 gene, a gpd1 deletion cassette, which is prepared in Example 1.2 in the same manner as the pdc1 deletion cassette and the cyb2 deletion cassette were prepared, and the above pdc1 and cyb2-deleted competent cell were mixed with 50% of polyethylene glycol and a single stranded carrier DNA and reacted in a water tub for about 1 hour at 42° C., and then, the culture solution was plated onto a uracil-free minimal agar plate (including YSD, 6.7 g/L of yeast nitrogen base without amino acids, and 1.4 g/L of amino acid dropout mix (-ura)) in a plate and cultured for 24 hours or more at 30° C. Ten colonies (a mutant strain) formed in the plate were selected, transferred to another uracil-free minimal agar plate, and, at the same time, cultured in a liquid medium including the same components contained in the uracil-free minimal medium to separate genome DNA from the strain by using a commonly used kit (Gentra Puregene Cell kit, Qiagen, USA). In order to confirm deletion of gpd1 by using the separated genome DNA of the mutant strain as a template, PCR was performed using primers of SEQ ID NOS: 47 and 48, and then, electrophoresis was performed on the obtained PCR product to confirm gpd1 deletion. As a result, *Saccharomyces cerevisiae* CEN.PK2-1D (Δ pdc1::ldh Δ cyb2::ldh Δ gpd1::ldh+ura3) was obtained.

Also, for additional gene deletion using the gene deletion vector, a URA3 gene as a selection marker of the gpd1 deletion cassette was removed by using the URA3 pop-out method as described above. *Saccharomyces cerevisiae* CEN.PK2-1D (Δ pdc1::ldh Δcyb2::ldh Δ gpd1::ldh+ura3) was inoculated in about 10 ml of a YPD liquid medium, cultured for about 18 hours at 30° C., plated onto a 5-FOA plate (including YSD, 6.7 g/L of yeast nitrogen base without amino acids, 1.4 g/L of an amino acid dropout mix, and 1 μg/L of 5-fluoroorotic acid) in a plate, and cultured for about 24 hours or more at 30° C. Ten colonies (a URA3 pop-out strain) formed in the plate were selected, transferred to another 5-FOA plate, and, at the same time, cultured in a YPD liquid to separate genome DNA from the strain by using a commonly used kit (Gentra Puregene Cell kit, Qiagen, USA). In order to confirm deletion of URA3 by using the separated genome DNA of the URA3 pop-out strain as a template, PCR was performed using primers of SEQ ID NOS: 47 and 48, and then electrophoresis was performed on the obtained PCR product to confirm URA3 deletion. As a result, *Saccharomyces cerevisiae* CEN.PK2-1D (Δ pdc1::ldh Δcyb2::ldh Δ gpd1::ldh) was obtained.

*Saccharomyces cerevisiae* CEN.PK2-1D (Δ pdc1::ldh Δ cyb2::ldhΔgpd1::ldh) was deposited in Korean Collection for Type Cultures (KCTC) on May 30, 2013, and received an accession number KCTC 12415BP.

Example 2

Preparation of a Gene Expression Vector Encoding TPI 1 and Preparation of *Saccharomyces cerevisiae* Introduced with Gene Encoding TPI 1

In order to prepare a lactate production strain with an enhanced carbon flux in the corresponding process, TPI with a polypeptide activity converting DHAP to GA3P was overexpressed or TPI of an exogenous cell was introduced.

(2.1) Preparation of a Gene Expression Vector Encoding TPI 1

A gene encoding TPI 1 (S. TPI1) of SEQ ID NO: 10 was amplified by performing PCR using gDNA (genomic DNA) of *Saccharomyces cerevisiae* as a template and primer sequences of SEQ ID NOS: 49 and 50.

Figure 4:
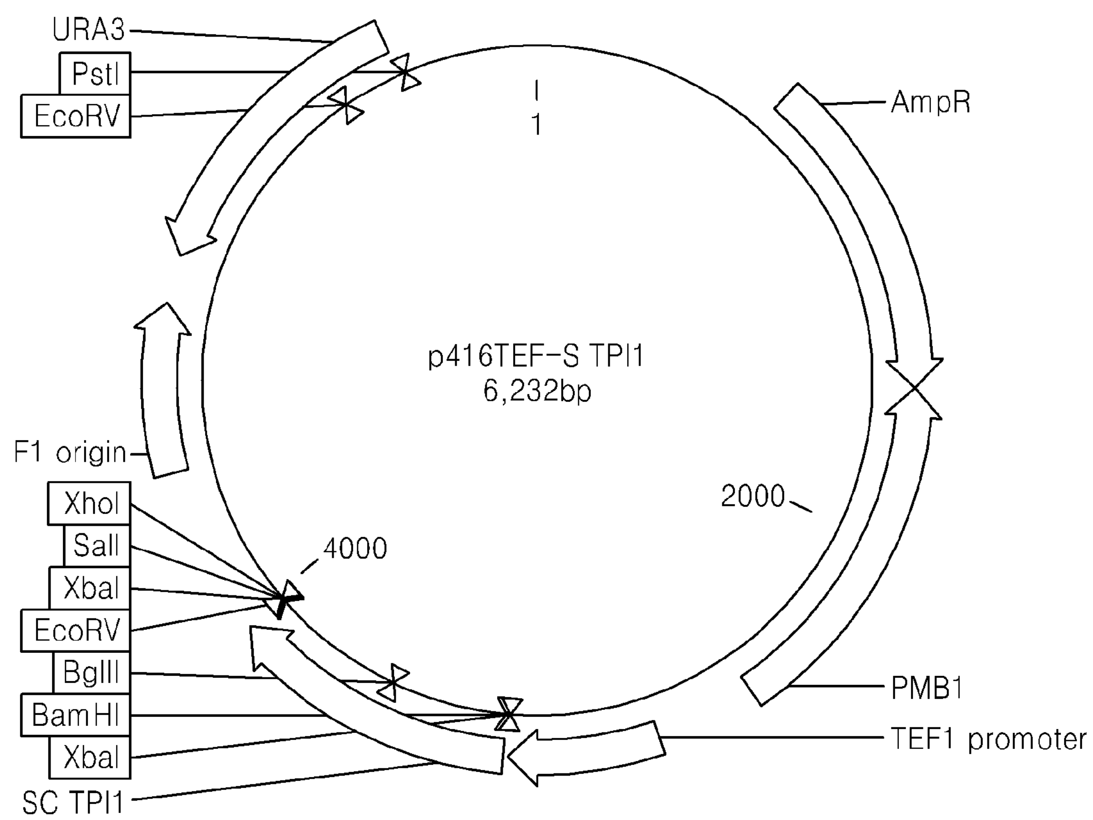
FIG. 4 is a schematic illustrating a p416TEF-S.TPI1 vector.

The resulting gene encoding TPI 1 derived from *Saccharomyces cerevisiae* was introduced to a p416 TEF plasmid (ATCC catalog #87368), which is a low copy number centromeric plasmid by using a restriction enzyme BamHI/SalI to prepare p416 TEF-S.TPI1. FIG. 4 is a view illustrating a p416TEF-S.TPI1 vector.

Also, a gene encoding TPI 1 was amplified by performing PCR using gDNA of *Trypanosoma brucei* as a template and primers of sequences of SEQ ID NOS: 51 and 52.

Figure 5:
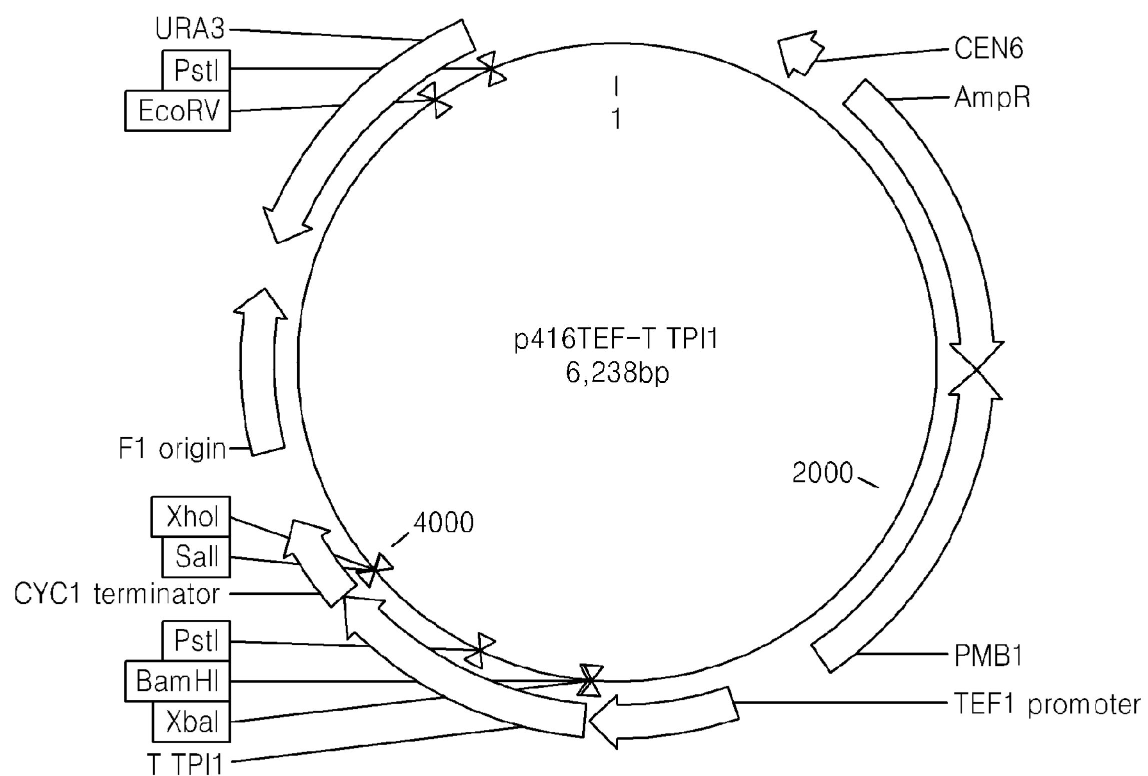
FIG. 5 is a schematic illustrating a p416TEF-T.TPI1 vector.

The resulting gene encoding TPI 1 derived from *Trypanosoma brucei* was introduced to a p416 TEF plasmid (ATCC catalog #87368), which is a low copy number centromeric plasmid by using a restriction enzyme BamHI/SalI to prepare p416 TEF-T.TPI1. FIG. 5 is a view illustrating a p416TEF-T.TPI1 vector.

Also, a gene encoding TPI 1(R. TPI1) of SEQ ID NO: 13 was amplified by performing PCR using gDNA of a rabbit muscle cell as a template and primers of sequences of SEQ ID NOS: 53 and 54.

Figure 6:
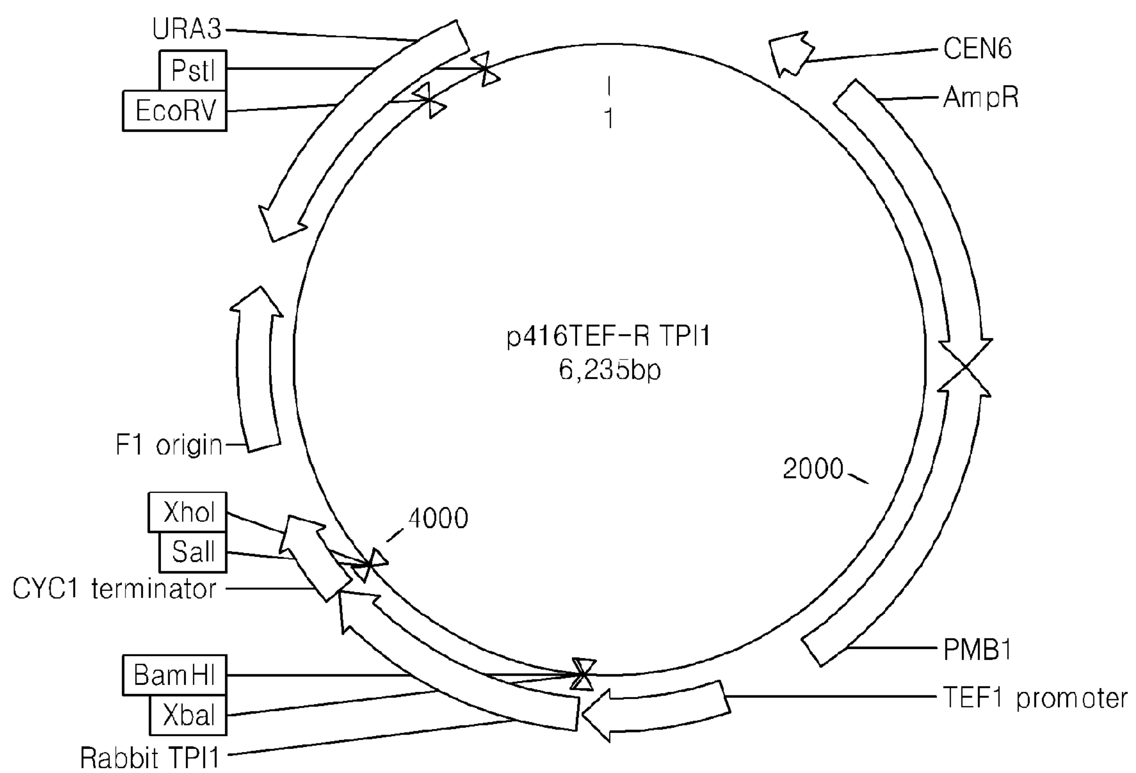
FIG. 6 illustrates a p416TEF-R.TPI1 vector.

The resulting gene encoding TPI 1 derived from a rabbit muscle cell was introduced to a p416 TEF plasmid (ATCC catalog #87368), which is a low copy number centromeric plasmid by using a restriction enzyme BamHI/SalI to prepare p416 TEF-R.TPI1. FIG. 6 is a view illustrating a p416TEF-R.TPI1 vector.

(2.2) Preparation of *Saccharomyces cerevisiae* Containing a Gene Encoding a Version of TPI1

The KCTC12415BP strain prepared in Example 2 was plated onto a YPD agar plate (including 10 g of yeast extract, 20 g of peptone, and 20 g of glucose) and incubated for 24 hours at 30° C., and then, a colony obtained therefrom was inoculated in about 10 ml of a YPD liquid medium and cultured for about 18 hours at 30° C. The sufficiently grown culture solution was inoculated in about 50 ml of a YPD liquid medium contained in a 250 ml-flask at a concentration of 1% (v/v) and cultured in an incubator at a rate of about 230 rpm and at 30° C.

After about 4 to 5 hours, when the $OD_{600}$ reached about 0.5, the culture was centrifuged at a rate of about 4,500 rpm for about 10 minutes to obtain cells, and the cells were resuspended in a lithium acetate solution at a concentration of about 100 mM. Then, the cells were obtained by performing centrifugation at a rate of about 4,500 rpm for about 10 minutes, resuspended in a lithium acetate solution at a concentration of about 1 M including about 15% of glycerol, and then divided into 100 ul aliquots each.

Each of p416 TEF-S.TPI1, p416 TEF-T.TPI1, and p416 TEF-R.TPI1 prepared in Example 2.1 and the above competent cell were mixed with 50% of polyethylene glycol and a single stranded carrier DNA and reacted in a water tub for about 1 hour at 42° C., and then, the culture solution was spread on a uracil-free minimal agar plate (including YSD, 6.7 g/L of yeast nitrogen base without amino acids, and 1.4 g/L of amino acid dropout mix (-ura)) and grown for about 24 hours or more at 30° C. Ten colonies (mutant strains) grown on the plate were selected, patched onto the fresh YSD (-ura) agar plate, and at the same time inoculated into a liquid YSD (-ura) medium to confirm that the p416 TEF-S.TPI1, p416 TEF-T.TPI1, and p416 TEF-R.TPI1 were introduced into each of the strains.

Example 3

Lactate Production Using the Genetically Engineered *S. cerevisiae*

The culturing process described below was performed to evaluate lactate product fermentation of the strain prepared in Example 2 and *Saccharomyces cerevisiae* CEN.PK2-1D KCTC12415BP as a control group.

The culture conditions including a first process and a second process below were formed in the liquid YSD (ura-), which is a uracil-free minimal liquid medium, in a 50 ml shaking flask.

The first process of the culture conditions was as follows. 50 ml of a YSD (ura-) liquid medium containing 4% glucose was cultured in a 250 ml shaking flask at a rate of about 250 rpm at about 30° C. The strain introduced with a TPI expression vector was inoculated into each of the shaking flasks, and the strain was grown until the strain reached a log-growth phase, i.e., about 15 hours to about 16 hours after the inoculation, or until the $OD_{600}$ reached about 5 to 8.

The second process of the culture conditions was as follows. 50 ml of the culture solution was centrifuged at a rate of about 3000 rpm for about 10 minutes to remove the supernatant. Then, the strain was resuspended in a 50 ml of fresh YSD (ura-) medium containing 8% glucose having 50 ml of the final volume, and the culture was moved to a 250 ml flask and grown at a rate of 80 rpm at 30° C. The culturing was performed until all the glucose was consumed, i.e., for about 24 hours to about 30 hours. Metabolites of the strain including lactate were measured by using HPLC to obtain lactate production yields. The results are shown in Table 4.

TABLE 4

| Origin of introduced TPI gene | $OD_{600}$ | Amount of lactate production (g/L) | Yield (%) |
|---|---|---|---|
| None | 7.23 | 22 | 33.8 |
| *Saccharomyces cerevisiae* | 7.97 | 22.5 | 37.1 |
| *Trypanosoma brucei* | 8.32 | 25 | 38.9 |
| Rabbit muscle cell | 8.11 | 25.5 | 40.4 |

As shown in Table 4, the *Saccharomyces cerevisiae* strains overexpressing the TPI genes derived from *Saccharomyces cerevisiae, Trypanosoma brucei*, and a rabbit muscle cell showed high lactate productivity and high lactate yield compared to those of *Saccharomyces cerevisiae* CEN.PK2-1D KCTC12415BP in which TPI gene is not introduced. Degrees of the increases in the productivity and yield were measured by comparing the levels of lactate productivity and yield of a control strain (*Saccharomyces cerevisiae* CEN.PK2-1D KCTC12415BP). Yield of lactate was calculated as a percent of the amount of produced lactate divided by the amount of consumed glucose, and the results are shown in Table 4.

Figure 7:
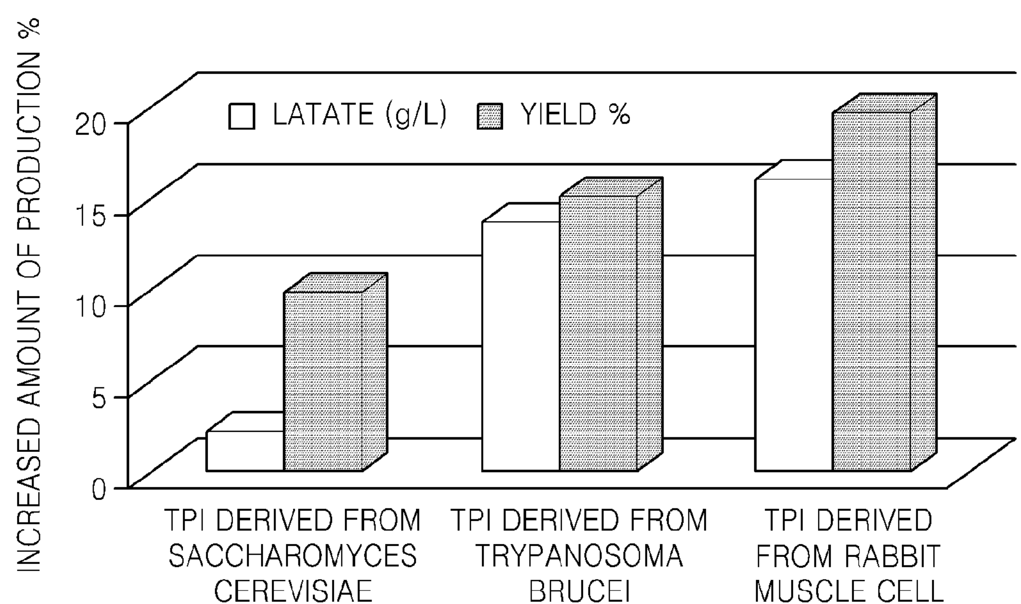
FIG. 7 is a graph illustrating amount of lactate produced (g/L) and lactate production yield (%) from genetically engineered *Saccharomyces cerevisiae* CEN.PK2-1D KCTC12415BP compared to *Saccharomyces cerevisiae* CEN.PK2-1D KCTC12415BP that is not genetically engineered when polynucleotides encoding triose-phosphate isomerase (TPI) derived from *Saccharomyces cerevisiae*, TPI derived from *Trypanosoma brucei*, and TPI derived from a rabbit muscle cell are individually introduced to *Saccharomyces cerevisiae* CEN.PK2-1D KCTC12415BP.

Also, the lactate productivity and yield of the *Saccharomyces cerevisiae* strains overexpressing the TPI genes derived from *Saccharomyces cerevisiae, Trypanosoma brucei*, and a rabbit muscle cell compared to the lactate productivity and yield of *Saccharomyces cerevisiae* CEN.PK2-1D KCTC12415BP are shown in FIG. 7 and Table 5. FIG. 7 is a view of lactate productivity and a lactate production yield (%) of genetically engineered *Saccharomyces cerevisiae* CEN.PK2-1D KCTC12415BP compared to *Saccharomyces cerevisiae* CEN.PK2-1D KCTC12415BP that is not genetically engineered when polynucleotides encoding TPI derived from *Saccharomyces cerevisiae*, TPI derived from *Trypanosoma brucei*, and TPI derived from a rabbit muscle cell are introduced to *Saccharomyces cerevisiae* CEN.PK2-1 D KCTC12415BP.

TABLE 5

| Origin of TPI gene | Production Increase (%) | Yield Increase (%) |
|---|---|---|
| *Saccharomyces cerevisiae* | 2.3 | 9.8 |
| *Trypanosoma brucei* | 13.6 | 15.1 |
| Rabbit muscle | 15 | 19.5 |

As shown in FIG. 1 and Table 5, *S. cerevisiae* strains overexpressing TPI gene derived from *Saccharomyces cerevisiae, Trypanosoma brucei*, and a rabbit muscle cell showed an increasingly high lactate productivity and lactate production yield, in that order.

[Accession Number]

Research Center Name: Korean Collection for Type Cultures (KTCT)

Accession Number: KCTC 12415BP

Accession Date: May 30, 2013

As described above, according to the one or more of the above embodiments of the present invention, a genetically engineered yeast cell may produce lactate in a high yield, a vector may be used in a method of preparing a yeast cell capable of producing lactate in a high yield, a yeast cell capable of producing lactate in a high yield may be prepared by using a method of preparing a microorganism, and lactate may be produced in a high yield by using a method of producing lactate.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A genetically engineered yeast cell capable of producing lactate, wherein the yeast cell has an exogenous gene encoding triose-phosphate isomerase (TPI) and an increased triose-phosphate isomerase (TPI) activity compared to a parent yeast cell, and the yeast cell further has an exogenous polynucleotide encoding a polypeptide that converts pyruvate to lactate and increased activity of converting pyruvate to lactate compared to a parent yeast cell.

2. The genetically engineered yeast cell of claim 1, wherein the yeast cell is *Saccharomyces* genus, *Kluyveromyces* genus, *Candida* genus, *Pichia* genus, *Issatchenkia* genus, *Debaryomyces* genus, *Zygosaccharomyces* genus, or *Saccharomycopsis* genus.

3. The genetically engineered yeast cell of claim 1, wherein the TPI gene is a homologous gene.

4. The genetically engineered yeast cell of claim 1, wherein the TPI gene is a heterologous gene.

5. The genetically engineered yeast cell of claim 1, wherein the TPI is from *Saccharomyces cerevisiae, Trypanosoma brucei*, or a rabbit.

6. The genetically engineered yeast cell of claim 1, wherein the TPI has 60% or more sequence identity with any one of SEQ ID NOS: 1 to 9.

7. The genetically engineered yeast cell of claim 1, wherein the gene encoding TPI comprises a nucleotide sequence selected from SEQ ID NOS: 10 to 13.

8. A method of producing lactate comprising
culturing the yeast cell of claim 1; and
collecting lactate from the culture.

9. A method of preparing a yeast cell of claim 1, wherein the method comprises introducing a TPI gene in to the yeast cell, thereby increasing the copy number of a TPI gene in the yeast cell.

10. The method of claim 9, wherein the TPI gene is a heterologous gene.

11. The method of claim 10, wherein the TPI gene is from *Trypanosoma brucei*, or a rabbit.

12. The method of claim 9, wherein the TPI gene is a homologous gene, and the gene is from *Saccharomyces cerevisiae.*

13. The genetically engineered yeast cell of claim 1, wherein the TPI has 90% or more sequence identity with any one of SEQ ID NOS: 1 to 9.

14. The genetically engineered yeast cell of claim 1, wherein the genetically engineered yeast cell produces lactate at a percent yield of 34% or greater.

* * * * *

```
                         SEQUENCE LISTING

<160> NUMBER OF SEQ ID NOS: 54

<210> SEQ ID NO 1
<211> LENGTH: 248
<212> TYPE: PRT
<213> ORGANISM: Saccharomyces cerevisiae

<400> SEQUENCE: 1

Met Ala Arg Thr Phe Phe Val Gly Gly Asn Phe Lys Leu Asn Gly Ser
 1               5                  10                  15

Lys Gln Ser Ile Lys Glu Ile Val Glu Arg Leu Asn Thr Ala Ser Ile
            20                  25                  30

Pro Glu Asn Val Glu Val Val Ile Cys Pro Pro Ala Thr Tyr Leu Asp
        35                  40                  45

Tyr Ser Val Ser Leu Val Lys Lys Pro Gln Val Thr Val Gly Ala Gln
    50                  55                  60

Asn Ala Tyr Leu Lys Ala Ser Gly Ala Phe Thr Gly Glu Asn Ser Val
65                  70                  75                  80

Asp Gln Ile Lys Asp Val Gly Ala Lys Trp Val Ile Leu Gly His Ser
                85                  90                  95

Glu Arg Arg Ser Tyr Phe His Glu Asp Asp Lys Phe Ile Ala Asp Lys
            100                 105                 110

Thr Lys Phe Ala Leu Gly Gln Gly Val Gly Val Ile Leu Cys Ile Gly
        115                 120                 125

Glu Thr Leu Glu Glu Lys Lys Ala Gly Lys Thr Leu Asp Val Val Glu
    130                 135                 140

Arg Gln Leu Asn Ala Val Leu Glu Glu Val Lys Asp Trp Thr Asn Val
145                 150                 155                 160

Val Val Ala Tyr Glu Pro Val Trp Ala Ile Gly Thr Gly Leu Ala Ala
                165                 170                 175
```

```
Thr Pro Glu Asp Ala Gln Asp Ile His Ala Ser Ile Arg Lys Phe Leu
            180                 185                 190

Ala Ser Lys Leu Gly Asp Lys Ala Ala Ser Glu Leu Arg Ile Leu Tyr
        195                 200                 205

Gly Gly Ser Ala Asn Gly Ser Asn Ala Val Thr Phe Lys Asp Lys Ala
    210                 215                 220

Asp Val Asp Gly Phe Leu Val Gly Gly Ala Ser Leu Lys Pro Glu Phe
225                 230                 235                 240

Val Asp Ile Ile Asn Ser Arg Asn
                245


<210> SEQ ID NO 2
<211> LENGTH: 248
<212> TYPE: PRT
<213> ORGANISM: Saccharomyces cerevisiae
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (107)..(107)
<223> OTHER INFORMATION: Xaa can be any naturally occurring amino acid

<400> SEQUENCE: 2

Met Ala Arg Thr Phe Phe Val Gly Gly Asn Phe Lys Leu Asn Gly Ser
 1               5                  10                  15

Lys Gln Ser Ile Lys Glu Ile Val Glu Arg Leu Asn Thr Ala Ser Ile
            20                  25                  30

Pro Glu Xaa Val Glu Val Val Ile Cys Pro Pro Ala Thr Tyr Leu Asp
        35                  40                  45

Tyr Ser Val Ser Leu Val Lys Lys Pro Gln Val Thr Val Gly Ala Gln
    50                  55                  60

Asn Ala Tyr Leu Lys Ala Ser Gly Ala Phe Thr Gly Glu Asn Ser Val
65                  70                  75                  80

Asp Gln Ile Lys Asp Val Gly Ala Lys Trp Val Ile Leu Gly His Ser
                85                  90                  95

Glu Arg Arg Ser Tyr Phe His Glu Asp Asp Xaa Phe Ile Ala Asp Lys
            100                 105                 110

Thr Lys Phe Ala Leu Gly Gln Gly Val Gly Val Ile Leu Cys Ile Gly
        115                 120                 125

Glu Thr Leu Glu Glu Lys Lys Ala Gly Lys Thr Leu Asp Val Val Glu
    130                 135                 140

Arg Gln Leu Asn Ala Val Leu Glu Glu Val Lys Asp Trp Thr Asn Val
145                 150                 155                 160

Val Val Ala Tyr Glu Pro Val Trp Ala Ile Gly Thr Gly Leu Ala Ala
                165                 170                 175

Thr Pro Glu Asp Ala Gln Asp Ile His Ala Ser Ile Arg Lys Phe Leu
            180                 185                 190

Ala Ser Lys Leu Gly Asp Lys Ala Ala Ser Glu Leu Arg Ile Leu Tyr
        195                 200                 205

Gly Gly Ser Ala Asn Gly Ser Asn Ala Val Thr Phe Lys Asp Lys Ala
    210                 215                 220

Asp Val Asp Gly Phe Leu Val Gly Gly Ala Ser Leu Lys Pro Glu Phe
225                 230                 235                 240

Val Asp Ile Ile Asn Ser Arg Asn
                245
```

```
<210> SEQ ID NO 3
<211> LENGTH: 252
<212> TYPE: PRT
<213> ORGANISM: Saccharomyces cerevisiae

<400> SEQUENCE: 3

Met Ala Arg Thr Phe Phe Val Gly Gly Asn Phe Lys Leu Asn Gly Ser
 1               5                  10                  15

Lys Gln Ser Ile Lys Glu Ile Val Glu Arg Leu Asn Thr Ala Ser Ile
            20                  25                  30

Pro Glu Asn Val Glu Val Val Ile Cys Pro Pro Ala Thr Tyr Leu Asp
        35                  40                  45

Tyr Ser Val Ser Leu Val Lys Lys Pro Gln Val Thr Val Gly Ala Gln
    50                  55                  60

Asn Ala Tyr Leu Lys Ala Ser Gly Ala Phe Thr Gly Glu Asn Ser Val
65                  70                  75                  80

Asp Gln Ile Lys Asp Val Gly Ala Lys Trp Val Ile Leu Gly His Ser
                85                  90                  95

Glu Arg Arg Ser Tyr Phe His Glu Asp Asp Lys Phe Ile Ala Asp Lys
            100                 105                 110

Thr Lys Phe Ala Leu Gly Gln Gly Val Gly Val Ile Leu Cys Ile Gly
        115                 120                 125

Glu Thr Leu Glu Glu Lys Lys Ala Gly Lys Thr Leu Asp Val Val Glu
    130                 135                 140

Arg Gln Leu Asn Ala Val Leu Glu Glu Val Lys Asp Trp Thr Asn Val
145                 150                 155                 160

Val Val Ala Tyr Glu Pro Val Trp Ala Ile Gly Thr Gly Leu Ala Ala
                165                 170                 175

Thr Pro Glu Asp Ala Gln Asp Ile His Ala Ser Ile Arg Lys Phe Leu
            180                 185                 190

Ala Ser Lys Leu Gly Asp Lys Ala Ala Ser Glu Leu Arg Ile Leu Tyr
        195                 200                 205

Gly Gly Ser Ala Asn Gly Ser Asn Ala Val Thr Phe Lys Asp Lys Ala
    210                 215                 220

Asp Val Asp Gly Phe Leu Val Gly Gly Ala Ser Leu Lys Pro Glu Phe
225                 230                 235                 240

Val Asp Ile Ile Asn Ser Arg Lys Leu Arg Leu Ile
                245                 250


<210> SEQ ID NO 4
<211> LENGTH: 248
<212> TYPE: PRT
<213> ORGANISM: Saccharomyces cerevisiae

<400> SEQUENCE: 4

Met Ala Arg Thr Phe Phe Val Gly Gly Asn Phe Lys Leu Asn Gly Ser
 1               5                  10                  15

Lys Gln Ser Ile Lys Glu Ile Val Glu Arg Leu Asn Thr Ala Ser Ile
            20                  25                  30

Pro Glu Asn Val Glu Val Val Ile Cys Pro Pro Ala Ile Tyr Leu Asp
        35                  40                  45

Tyr Ser Val Ser Leu Val Lys Lys Pro Gln Val Thr Val Gly Ala Gln
    50                  55                  60

Asn Ala Tyr Leu Lys Ala Ser Gly Ala Phe Thr Gly Glu Asn Ser Val
65                  70                  75                  80
```

```
Asp Glu Ile Lys Asp Val Gly Ala Lys Trp Val Val Leu Gly His Ser
                85                  90                  95

Glu Arg Arg Ser Tyr Phe His Glu Asp Asp Lys Phe Val Ala Glu Lys
            100                 105                 110

Thr Lys Phe Ala Leu Gly Gln Gly Val Gly Val Ile Leu Cys Ile Gly
        115                 120                 125

Glu Thr Leu Glu Glu Lys Lys Ala Gly Lys Thr Leu Asp Val Val Glu
    130                 135                 140

Arg Gln Leu Asn Ala Val Leu Glu Glu Val Lys Asp Trp Thr Asn Val
145                 150                 155                 160

Val Val Ala Tyr Glu Pro Val Trp Ala Ile Gly Ser Gly Leu Ala Ala
                165                 170                 175

Thr Pro Glu Asp Ala Gln Asp Ile His Ala Ser Ile Arg Lys Phe Leu
            180                 185                 190

Ala Ser Lys Leu Gly Asp Lys Thr Ala Ser Glu Leu Arg Ile Leu Tyr
        195                 200                 205

Gly Gly Ser Ala Asn Gly Ser Asn Ala Val Thr Phe Lys Thr Lys Ala
    210                 215                 220

Asp Val Asp Gly Phe Leu Val Gly Gly Ala Ser Leu Lys Pro Glu Phe
225                 230                 235                 240

Val Asp Ile Ile Asn Ser Arg Asn
                245


<210> SEQ ID NO 5
<211> LENGTH: 250
<212> TYPE: PRT
<213> ORGANISM: Trypanosoma brucei

<400> SEQUENCE: 5

Met Ser Lys Pro Gln Pro Ile Ala Ala Ala Asn Trp Lys Cys Asn Gly
 1               5                  10                  15

Ser Gln Gln Ser Leu Ser Glu Leu Ile Asp Leu Phe Asn Ser Thr Ser
            20                  25                  30

Ile Asn His Asp Val Gln Cys Val Val Ala Ser Thr Phe Val His Leu
        35                  40                  45

Ala Met Thr Lys Glu Arg Leu Ser His Pro Lys Phe Val Ile Ala Ala
    50                  55                  60

Gln Asn Ala Ile Ala Lys Ser Gly Ala Phe Thr Gly Glu Val Ser Leu
65                  70                  75                  80

Pro Ile Leu Lys Asp Phe Gly Val Asn Trp Ile Val Leu Gly His Ser
                85                  90                  95

Glu Arg Arg Ala Tyr Tyr Gly Glu Thr Asn Glu Ile Val Ala Asp Lys
            100                 105                 110

Val Ala Ala Ala Val Ala Ala Gly Phe Met Val Ile Ala Cys Ile Gly
        115                 120                 125

Glu Thr Leu Gln Glu Arg Glu Ser Gly Arg Thr Ala Val Val Val Leu
    130                 135                 140

Thr Gln Ile Ala Ala Ile Ala Lys Lys Leu Lys Lys Ala Asp Trp Ala
145                 150                 155                 160

Lys Val Val Ile Ala Tyr Glu Pro Val Trp Ala Ile Gly Thr Gly Lys
                165                 170                 175

Val Ala Thr Pro Gln Gln Ala Gln Glu Ala His Ala Leu Ile Arg Ser
            180                 185                 190

Trp Val Ser Ser Lys Ile Gly Ala Asp Val Ala Gly Glu Leu Arg Ile
```

```
        195                 200                 205

Leu Tyr Gly Gly Ser Val Asn Gly Lys Asn Ala Arg Thr Leu Tyr Gln
    210                 215                 220

Gln Arg Asp Val Asn Gly Phe Leu Val Gly Gly Ala Ser Leu Lys Pro
225                 230                 235                 240

Glu Phe Val Asp Ile Ile Lys Ala Thr Gln
                245                 250


<210> SEQ ID NO 6
<211> LENGTH: 250
<212> TYPE: PRT
<213> ORGANISM: Trypanosoma brucei

<400> SEQUENCE: 6

Met Ser Lys Pro Gln Pro Ile Ala Ala Ala Asn Trp Lys Cys Asn Gly
 1               5                  10                  15

Ser Gln Gln Ser Leu Ser Glu Leu Ile Asp Leu Phe Asn Ser Thr Ser
            20                  25                  30

Ile Asn His Asp Val Gln Cys Val Val Ala Ser Thr Phe Val His Leu
        35                  40                  45

Ala Met Thr Lys Glu Arg Leu Ser His Pro Lys Phe Val Ile Ala Ala
    50                  55                  60

Gln Asn Ala Ile Ala Lys Ser Gly Ala Phe Thr Gly Glu Val Ser Leu
65                  70                  75                  80

Pro Ile Leu Lys Asp Phe Gly Val Asn Trp Ile Val Leu Gly His Ser
                85                  90                  95

Glu Arg Arg Ala Tyr Tyr Gly Glu Thr Asn Glu Ile Val Ala Asp Lys
            100                 105                 110

Val Ala Ala Ala Val Ala Ser Gly Phe Met Val Ile Ala Cys Ile Gly
        115                 120                 125

Glu Thr Leu Gln Glu Arg Glu Ser Gly Arg Thr Ala Val Val Val Leu
    130                 135                 140

Thr Gln Ile Ala Ala Ile Ala Lys Lys Leu Lys Lys Ala Asp Trp Ala
145                 150                 155                 160

Lys Val Val Ile Ala Tyr Glu Pro Val Trp Ala Ile Gly Thr Gly Lys
                165                 170                 175

Val Ala Thr Pro Gln Gln Ala Gln Glu Ala His Ala Leu Ile Arg Ser
            180                 185                 190

Trp Val Ser Ser Lys Ile Gly Ala Asp Val Ala Gly Glu Leu Arg Ile
        195                 200                 205

Leu Tyr Gly Gly Ser Val Asn Gly Lys Asn Ala Arg Thr Leu Tyr Gln
    210                 215                 220

Gln Arg Asp Val Asn Gly Phe Leu Val Gly Gly Ala Ser Leu Lys Pro
225                 230                 235                 240

Glu Phe Val Asp Ile Ile Lys Ala Thr Gln
                245                 250


<210> SEQ ID NO 7
<211> LENGTH: 355
<212> TYPE: PRT
<213> ORGANISM: Trypanosoma brucei

<400> SEQUENCE: 7

Met Glu Ala Glu Thr Ser Lys Ile Ser Glu Val Pro Leu Pro Ile Pro
 1               5                  10                  15

Ile Gly Ile Asn Gly Phe Gly Ala Val Gly Arg Ala Val Leu Phe Ala
```

```
            20                  25                  30

Ser Met Thr Glu Pro Gln Val Thr Val Val Ala Val Asn Asp Phe Ser
        35                  40                  45

Val Ser Ile Asn Tyr Val Leu Tyr Val Leu Gln Asn Glu Ser Pro Leu
    50                  55                  60

Ser Ala Glu Asp Lys Ala Ser Leu Thr Val Val Gly Glu Tyr Ile Phe
65                  70                  75                  80

Tyr Arg Gly Thr Glu Arg Ile Arg Val Thr Gln Lys His Asp Leu Val
                85                  90                  95

Asp Ile Ala Trp Arg Asp Ala Gly Val Ser Tyr Val Val Glu Cys Thr
            100                 105                 110

Gly Phe Thr Ser Thr Arg Asp Arg Cys Trp Gly His Leu Thr Ser Gly
        115                 120                 125

Ala Arg Gly Val Leu Val Ala Gly Gln Ser Gly Asp Ala Pro Ala Ile
    130                 135                 140

Val Ala Gly Val Asn Asp Ser Asp Leu Ser Lys Ile Gln Pro Ile Ile
145                 150                 155                 160

Cys Ser Gly Ala Pro Leu Ala Val Ala Leu Ala Pro Phe Ile Arg Ile
                165                 170                 175

Leu His Glu Ser Phe Gly Val Glu Asp Cys Ser Tyr Thr Ala Ile His
            180                 185                 190

Ala Ile Gln Pro Val Glu Pro Asn Ala Ala Arg Ser Ala Asn Ser Gln
        195                 200                 205

Asp Trp Arg Gln Thr Arg Val Thr Leu Asp Ser Ile Thr Pro Tyr Ala
    210                 215                 220

His Thr Gly Met Thr Thr Phe Cys Lys Leu Met Pro Thr Leu Ser Ser
225                 230                 235                 240

Arg Ile Thr Gly Ser Ala Phe Gln Val Pro Val Thr Lys Gly Cys Ala
                245                 250                 255

Ile Asp Met Leu Leu Arg Phe Lys Gln Pro Val Ala Lys Glu Ser Val
            260                 265                 270

Asp Glu Ala Leu Ile Glu Ala Ser Lys Asp Arg Leu Lys Asp Val Leu
        275                 280                 285

Phe Val Ser Lys Arg Asp Phe Ile Ser Arg Asp Leu Leu Pro Asp Gly
    290                 295                 300

Lys Leu Cys Tyr Asp Pro Ser Ala Ser Gln Cys Val Arg Glu Gly Glu
305                 310                 315                 320

Leu Tyr Lys Phe Thr Leu Trp Phe Asp Leu Glu Arg Ser Phe Ala Lys
                325                 330                 335

Arg Leu Ile Ser Leu Ile Pro Val Met Asn Asp Ala Asp Ala Lys Lys
            340                 345                 350

Asn Asn Val
        355


<210> SEQ ID NO 8
<211> LENGTH: 249
<212> TYPE: PRT
<213> ORGANISM: Oryctolagus cuniculus

<400> SEQUENCE: 8

Met Ala Pro Ser Arg Lys Phe Phe Val Gly Gly Asn Trp Lys Met Asn
 1               5                  10                  15

Gly Arg Lys Lys Asn Leu Gly Glu Leu Ile Thr Thr Leu Asn Ala Ala
            20                  25                  30
```

```
Lys Val Pro Ala Asp Thr Glu Val Val Cys Ala Pro Pro Thr Ala Tyr
        35                  40                  45

Ile Asp Phe Ala Arg Gln Lys Leu Asp Pro Lys Ile Ala Val Ala Ala
    50                  55                  60

Gln Asn Cys Tyr Lys Val Thr Asn Gly Ala Phe Thr Gly Glu Ile Ser
65                  70                  75                  80

Pro Gly Met Ile Lys Asp Cys Gly Ala Thr Trp Val Val Leu Gly His
                85                  90                  95

Ser Glu Arg Arg His Val Phe Gly Glu Ser Asp Glu Leu Ile Gly Gln
            100                 105                 110

Lys Val Ala His Ala Leu Ser Glu Gly Leu Gly Val Ile Ala Cys Ile
        115                 120                 125

Gly Glu Lys Leu Asp Glu Arg Glu Ala Gly Ile Thr Glu Lys Val Val
    130                 135                 140

Phe Glu Gln Thr Lys Val Ile Ala Asp Asn Val Lys Asp Trp Ser Lys
145                 150                 155                 160

Val Val Leu Ala Tyr Glu Pro Val Trp Ala Ile Gly Thr Gly Lys Thr
                165                 170                 175

Ala Thr Pro Gln Gln Ala Gln Glu Val His Glu Lys Leu Arg Gly Trp
            180                 185                 190

Leu Lys Ser Asn Val Ser Asp Ala Val Ala Gln Ser Thr Arg Ile Ile
        195                 200                 205

Tyr Gly Gly Ser Val Thr Gly Ala Thr Cys Lys Glu Leu Ala Ser Gln
    210                 215                 220

Pro Asp Val Asp Gly Phe Leu Val Gly Gly Ala Ser Leu Lys Pro Glu
225                 230                 235                 240

Phe Val Asp Ile Ile Asn Ala Lys Gln
                245


<210> SEQ ID NO 9
<211> LENGTH: 288
<212> TYPE: PRT
<213> ORGANISM: Oryctolagus cuniculus

<400> SEQUENCE: 9

Met Ala Gly Thr Gly Gln Glu Ala Glu Phe Arg Phe Ser Ala Phe Tyr
 1               5                  10                  15

Ile Ser Arg Gln Arg Pro Gln Pro Arg Pro His Gly Gly Thr Asp Leu
            20                  25                  30

Gln Cys Ala Gly Pro Ser Ala Met Ala Pro Ser Arg Lys Phe Phe Val
        35                  40                  45

Gly Gly Asn Trp Lys Met Asn Gly Arg Lys Lys Asn Leu Gly Glu Leu
    50                  55                  60

Ile Thr Thr Leu Asn Ala Ala Lys Val Pro Ala Asp Thr Glu Val Val
65                  70                  75                  80

Cys Ala Pro Pro Thr Ala Tyr Ile Asp Phe Ala Arg Gln Lys Leu Asp
                85                  90                  95

Pro Lys Ile Ala Val Ala Ala Gln Asn Cys Tyr Lys Val Thr Asn Gly
            100                 105                 110

Ala Phe Thr Gly Glu Ile Ser Pro Gly Met Ile Lys Asp Cys Gly Ala
        115                 120                 125

Thr Trp Val Val Leu Gly His Ser Glu Arg Arg His Val Phe Gly Glu
    130                 135                 140

Ser Asp Glu Leu Ile Gly Gln Lys Val Ala His Ala Leu Ser Glu Gly
145                 150                 155                 160
```

```
Leu Gly Val Ile Ala Cys Ile Gly Glu Lys Leu Asp Glu Arg Glu Ala
                165                 170                 175

Gly Ile Thr Glu Lys Val Val Phe Glu Gln Thr Lys Val Ile Ala Asp
            180                 185                 190

Asn Val Lys Asp Trp Ser Lys Val Val Leu Ala Tyr Glu Pro Val Trp
        195                 200                 205

Ala Ile Gly Thr Gly Lys Thr Ala Thr Pro Gln Gln Ala Gln Glu Val
    210                 215                 220

His Glu Lys Leu Arg Gly Trp Leu Lys Ser Asn Val Ser Asp Ala Val
225                 230                 235                 240

Ala Gln Ser Thr Arg Ile Ile Tyr Gly Gly Ser Val Thr Gly Ala Thr
                245                 250                 255

Cys Lys Glu Leu Ala Ser Gln Pro Asp Val Asp Gly Phe Leu Val Gly
            260                 265                 270

Gly Ala Ser Leu Lys Pro Glu Phe Val Asp Ile Ile Asn Ala Lys Gln
        275                 280                 285
```

<210> SEQ ID NO 10
<211> LENGTH: 747
<212> TYPE: DNA
<213> ORGANISM: Saccharomyces cerevisiae

<400> SEQUENCE: 10

```
atggctagaa ctttctttgt cggtggtaac tttaaattaa acggttccaa acaatccatt      60

aaggaaattg ttgaaagatt gaacactgct tctatcccag aaaatgtcga agttgttatc     120

tgtcctccag ctacctactt agactactct gtctctttgg ttaagaagcc acaagtcact     180

gtcggtgctc aaaacgccta cttgaaggct tctggtgctt tcaccggtga aaactccgtt     240

gaccaaatca aggatgttgg tgctaagtgg gttattttgg gtcactccga aagaagatct     300

tacttccacg aagatgacaa gttcattgct gacaagacca agttcgcttt aggtcaaggt     360

gtcggtgtca tcttgtgtat cggtgaaact ttggaagaaa agaaggccgg taagactttg     420

gatgttgttg aaagacaatt gaacgctgtc ttggaagaag ttaaggactg gactaacgtc     480

gttgtcgctt acgaaccagt ctgggccatt ggtaccggtt tggctgctac tccagaagat     540

gctcaagata ttcacgcttc catcagaaag ttcttggctt ccaagttggg tgacaaggct     600

gccagcgaat tgagaatctt atacggtggt tccgctaacg gtagcaacgc cgttaccttc     660

aaggacaagg ctgatgtcga tggtttcttg gtcggtggtg cttctttgaa gccagaattt     720

gttgatatca tcaactctag aaactaa                                        747
```

<210> SEQ ID NO 11
<211> LENGTH: 1648
<212> TYPE: DNA
<213> ORGANISM: Saccharomyces cerevisiae

<400> SEQUENCE: 11

```
gaatccatca atagatacgt cctgaggacc gtgctaccca aatggactga ttgtgaggga      60

gacctaacta catagtgttt aagattacgg atatttaact tacttagaat aatgccattt     120

ttttgagtta taataatcct acgttagtgt gagcgggatt taaactgtga ggaccttaat     180

acattcagac acttctgacg gtatcaccct acttattccc ttcgagatta tatctaggaa     240

cccatcaggt tggtggaaga ttacccgttc taagactttt cagcttcctc tattgatgtt     300

acacttggac accccttttc tggcatccag tttttaatct tcagtggcat gtgagattct     360
```

```
ccgaaattaa ttaaagcaat cacacaattc tctcggatac cacctcggtt gaaactgaca    420

ggtggtttgt tacgcatgct aatgcaaagg agcctatata cctttggctc ggctgctgta    480

acagggaata taaagggcag cataatttag gagtttagtg aacttgcaac atttactatt    540

ttcccttctt acgtaaatat ttttcttttt aattctaaat caatcttttt caatttttttg   600

tttgtattct tttcttgctt aaatctataa ctacaaaaaa cacatacata aactaaaaat    660

ggctagaact ttctttgtcg gtggtaactt taaattaaac ggttccaaac aatccattaa    720

ggaaattgtt gaaagattga acactgcttc tatcccagaa aatgtcgaag ttgttatctg    780

tcctccagct acctacttag actactctgt ctctttggtt aagaagccac aagtcactgt    840

cggtgctcaa aacgcctact tgaaggcttc tggtgctttc accggtgaaa actccgttga    900

ccaaatcaag gatgttggtg ctaagtgggt tattttgggt cactccgaaa gaagatctta    960

cttccacgaa gatgacaagt tcattgctga caagaccaag ttcgctttag gtcaaggtgt   1020

cggtgtcatc ttgtgtatcg gtgaaacttt ggaagaaaag aaggccggta agactttgga   1080

tgttgttgaa agacaattga acgctgtctt ggaagaagtt aaggactgga ctaacgtcgt   1140

tgtcgcttac gaaccagtct gggccattgg taccggtttg gctgctactc cagaagatgc   1200

tcaagatatt cacgcttcca tcagaaagtt cttggcttcc aagttgggtg acaaggctgc   1260

cagcgaattg agaatcttat acggtggttc cgctaacggt agcaacgccg ttaccttcaa   1320

ggacaaggct gatgtcgatg gtttcttggt cggtggtgct tctttgaagc cagaatttgt   1380

tgatatcatc aactctagaa actaagatta atataattat ataaaaatat tatcttcttt   1440

tctttatatc tagtgttatg taaaataaat tgatgactac ggaaagcttt tttatattgt   1500

ttctttttca ttctgagcca cttaaatttc gtgaatgttc ttgtaaggga cggtagattt   1560

acaagtgata caacaaaaag caaggcgctt tttctaataa aaagaagaaa agcatttaac   1620

aattgaacac ctctatatca acagaaga                                       1648


<210> SEQ ID NO 12
<211> LENGTH: 753
<212> TYPE: DNA
<213> ORGANISM: Trypanosoma brucei

<400> SEQUENCE: 12

atgtccaagc cacaacccat cgcagcagcc aactggaagt gcaacggctc ccaacagtct     60

ttgtcggagc ttattgatct gtttaactcc acaagcatca accacgacgt gcaatgcgta    120

gtggcctcca cctttgttca ccttgccatg acgaaggagc gtctttcaca ccccaaattt    180

gtgattgcgg cgcagaacgc cattgcaaag agcggtgcct tcaccggcga agtctccctg    240

cccatcctca aagatttcgg tgtcaactgg attgttctgg gtcactccga gcgccgcgca    300

tactatggtg agacaaacga gattgttgcg gacaaggttg ccgccgccgt tgctgctggt    360

ttcatggtta ttgcttgcat cggcgaaacg ctgcaggagc gtgaatcagg tcgcaccgct    420

gttgttgtgc tcacacagat cgctgctatt gctaagaaac tgaagaaggc tgactgggcc    480

aaagttgtca tcgcctacga acccgtttgg gccattggta ccggcaaggt ggcgacacca    540

cagcaagcgc aggaagccca cgcactcatc cgcagctggg tgagcagcaa gattggagca    600

gatgtcgcgg gagagctccg cattctttac ggcggttctg ttaatggaaa gaatgcgcgc    660

actctttacc aacagcgaga cgtcaacggc ttccttgttg gtggtgcctc actgaagcca    720

gaatttgtgg acatcatcaa agccactcag tga                                 753
```

<210> SEQ ID NO 13
<211> LENGTH: 750
<212> TYPE: DNA
<213> ORGANISM: Oryctolagus cuniculus

<400> SEQUENCE: 13
atggcgccct ccaggaaatt cttcgttggg ggcaactgga agatgaacgg aaggaagaag 60
aacctggggg agctcatcac caccctgaac gcagccaagg tgccggccga caccgaggtg 120
gtttgtgcac cccccactgc ctacattgac tttgcccggc agaaactgga tcccaagatt 180
gctgtggctg cacagaactg ctacaaagtg actaacgggg ccttcactgg ggagatcagc 240
cctggcatga tcaaagactg tggagccacg tgggtggtcc tgggccactc tgagaggagg 300
catgtctttg gggaatcaga tgagctgatt gggcagaaag tggcccacgc cctgtcagag 360
ggccttggtg tgattgcctg catcggggag aagctggatg aaagggaggc tggcatcacg 420
gagaaggtcg tgtttgagca aaccaaggtc atcgcagata acgtaaagga ctggagcaag 480
gttgtcctgg cctatgagcc tgtgtgggcc atcggaaccg gcaagactgc aacaccccaa 540
caggcccagg aagtccatga gaagctccga gggtggctca agtccaacgt ctctgacgct 600
gtggctcaga gtacccgcat catctacgga ggttctgtga ctggagcaac ctgcaaggaa 660
ctggcaagcc agcctgacgt ggatggcttc cttgtgggag gtgcttccct caaacctgaa 720
ttcgtggaca tcatcaatgc caaacaataa 750

<210> SEQ ID NO 14
<211> LENGTH: 563
<212> TYPE: PRT
<213> ORGANISM: Saccharomyces cerevisiae

<400> SEQUENCE: 14

Met Ser Glu Ile Thr Leu Gly Lys Tyr Leu Phe Glu Arg Leu Lys Gln
1 5 10 15

Val Asn Val Asn Thr Val Phe Gly Leu Pro Gly Asp Phe Asn Leu Ser
20 25 30

Leu Leu Asp Lys Ile Tyr Glu Val Glu Gly Met Arg Trp Ala Gly Asn
35 40 45

Ala Asn Glu Leu Asn Ala Ala Tyr Ala Ala Asp Gly Tyr Ala Arg Ile
50 55 60

Lys Gly Met Ser Cys Ile Ile Thr Thr Phe Gly Val Gly Glu Leu Ser
65 70 75 80

Ala Leu Asn Gly Ile Ala Gly Ser Tyr Ala Glu His Val Gly Val Leu
85 90 95

His Val Val Gly Val Pro Ser Ile Ser Ala Gln Ala Lys Gln Leu Leu
100 105 110

Leu His His Thr Leu Gly Asn Gly Asp Phe Thr Val Phe His Arg Met
115 120 125

Ser Ala Asn Ile Ser Glu Thr Thr Ala Met Ile Thr Asp Ile Ala Thr
130 135 140

Ala Pro Ala Glu Ile Asp Arg Cys Ile Arg Thr Thr Tyr Val Thr Gln
145 150 155 160

Arg Pro Val Tyr Leu Gly Leu Pro Ala Asn Leu Val Asp Leu Asn Val
165 170 175

Pro Ala Lys Leu Leu Gln Thr Pro Ile Asp Met Ser Leu Lys Pro Asn
180 185 190

Asp Ala Glu Ser Glu Lys Glu Val Ile Asp Thr Ile Leu Ala Leu Val
195 200 205

```
Lys Asp Ala Lys Asn Pro Val Ile Leu Ala Asp Ala Cys Cys Ser Arg
    210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
            340                 345                 350

Thr Pro Ala Asn Ala Ala Val Pro Ala Ser Thr Pro Leu Lys Gln Glu
        355                 360                 365

Trp Met Trp Asn Gln Leu Gly Asn Phe Leu Gln Glu Gly Asp Val Val
    370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Lys Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
            500                 505                 510

Ala Thr Thr Gly Glu Trp Asp Lys Leu Thr Gln Asp Lys Ser Phe Asn
        515                 520                 525

Asp Asn Ser Lys Ile Arg Met Ile Glu Ile Met Leu Pro Val Phe Asp
    530                 535                 540

Ala Pro Gln Asn Leu Val Glu Gln Ala Lys Leu Thr Ala Ala Thr Asn
545                 550                 555                 560

Ala Lys Gln
```

<210> SEQ ID NO 15
<211> LENGTH: 1692
<212> TYPE: DNA
<213> ORGANISM: Saccharomyces cerevisiae

<400> SEQUENCE: 15

```
atgtctgaaa ttactttggg taaatatttg ttcgaaagat taaagcaagt caacgttaac     60
```

```
accgttttcg gtttgccagg tgacttcaac ttgtccttgt tggacaagat ctacgaagtt    120

gaaggtatga gatgggctgg taacgccaac gaattgaacg ctgcttacgc cgctgatggt    180

tacgctcgta tcaagggtat gtcttgtatc atcaccacct tcggtgtcgg tgaattgtct    240

gctttgaacg gtattgccgg ttcttacgct gaacacgtcg gtgttttgca cgttgttggt    300

gtcccatcca tctctgctca agctaagcaa ttgttgttgc accacacctt gggtaacggt    360

gacttcactg ttttccacag aatgtctgcc aacatttctg aaaccactgc tatgatcact    420

gacattgcta ccgccccagc tgaaattgac agatgtatca gaaccactta cgtcacccaa    480

agaccagtct acttaggttt gccagctaac ttggtcgact tgaacgtccc agctaagttg    540

ttgcaaactc caattgacat gtctttgaag ccaaacgatg ctgaatccga aaaggaagtc    600

attgacacca tcttggcttt ggtcaaggat gctaagaacc cagttatctt ggctgatgct    660

tgttgttcca gacacgacgt caaggctgaa actaagaagt tgattgactt gactcaattc    720

ccagctttcg tcaccccaat gggtaagggt tccattgacg aacaacaccc aagatacggt    780

ggtgtttacg tcggtacctt gtccaagcca gaagttaagg aagccgttga atctgctgac    840

ttgattttgt ctgtcggtgc tttgttgtct gatttcaaca ccggttcttt ctcttactct    900

tacaagacca agaacattgt cgaattccac tccgaccaca tgaagatcag aaacgccact    960

ttcccaggtg tccaaatgaa attcgttttg caaaagttgt tgaccactat tgctgacgcc   1020

gctaagggtt acaagccagt tgctgtccca gctagaactc cagctaacgc tgctgtccca   1080

gcttctaccc cattgaagca agaatggatg tggaaccaat tgggtaactt cttgcaagaa   1140

ggtgatgttg tcattgctga aaccggtacc tccgctttcg gtatcaacca aaccactttc   1200

ccaaacaaca cctacggtat ctctcaagtc ttatggggtt ccattggttt caccactggt   1260

gctaccttgg gtgctgcttt cgctgctgaa gaaattgatc caaagaagag agttatctta   1320

ttcattggtg acggttcttt gcaattgact gttcaagaaa tctccaccat gatcagatgg   1380

ggcttgaagc catacttgtt cgtcttgaac aacgatggtt acaccattga aaagttgatt   1440

cacggtccaa aggctcaata caacgaaatt caaggttggg accacctatc cttgttgcca   1500

actttcggtg ctaaggacta tgaaacccac agagtcgcta ccaccggtga atgggacaag   1560

ttgacccaag acaagtcttt caacgacaac tctaagatca gaatgattga aatcatgttg   1620

ccagtcttcg atgctccaca aaacttggtt gaacaagcta agttgactgc tgctaccaac   1680

gctaagcaat aa                                                       1692
```

<210> SEQ ID NO 16
<211> LENGTH: 591
<212> TYPE: PRT
<213> ORGANISM: Saccharomyces cerevisiae

<400> SEQUENCE: 16

```
Met Leu Lys Tyr Lys Pro Leu Leu Lys Ile Ser Lys Asn Cys Glu Ala
 1               5                  10                  15

Ala Ile Leu Arg Ala Ser Lys Thr Arg Leu Asn Thr Ile Arg Ala Tyr
            20                  25                  30

Gly Ser Thr Val Pro Lys Ser Lys Ser Phe Glu Gln Asp Ser Arg Lys
        35                  40                  45

Arg Thr Gln Ser Trp Thr Ala Leu Arg Val Gly Ala Ile Leu Ala Ala
    50                  55                  60

Thr Ser Ser Val Ala Tyr Leu Asn Trp His Asn Gly Gln Ile Asp Asn
65                  70                  75                  80
```

```
Glu Pro Lys Leu Asp Met Asn Lys Gln Lys Ile Ser Pro Ala Glu Val
                85                  90                  95

Ala Lys His Asn Lys Pro Asp Asp Cys Trp Val Val Ile Asn Gly Tyr
            100                 105                 110

Val Tyr Asp Leu Thr Arg Phe Leu Pro Asn His Pro Gly Gly Gln Asp
        115                 120                 125

Val Ile Lys Phe Asn Ala Gly Lys Asp Val Thr Ala Ile Phe Glu Pro
    130                 135                 140

Leu His Ala Pro Asn Val Ile Asp Lys Tyr Ile Ala Pro Glu Lys Lys
145                 150                 155                 160

Leu Gly Pro Leu Gln Gly Ser Met Pro Pro Glu Leu Val Cys Pro Pro
                165                 170                 175

Tyr Ala Pro Gly Glu Thr Lys Glu Asp Ile Ala Arg Lys Glu Gln Leu
            180                 185                 190

Lys Ser Leu Leu Pro Pro Leu Asp Asn Ile Ile Asn Leu Tyr Asp Phe
        195                 200                 205

Glu Tyr Leu Ala Ser Gln Thr Leu Thr Lys Gln Ala Trp Ala Tyr Tyr
    210                 215                 220

Ser Ser Gly Ala Asn Asp Glu Val Thr His Arg Glu Asn His Asn Ala
225                 230                 235                 240

Tyr His Arg Ile Phe Phe Lys Pro Lys Ile Leu Val Asp Val Arg Lys
                245                 250                 255

Val Asp Ile Ser Thr Asp Met Leu Gly Ser His Val Asp Val Pro Phe
            260                 265                 270

Tyr Val Ser Ala Thr Ala Leu Cys Lys Leu Gly Asn Pro Leu Glu Gly
        275                 280                 285

Glu Lys Asp Val Ala Arg Gly Cys Gly Gln Gly Val Thr Lys Val Pro
    290                 295                 300

Gln Met Ile Ser Thr Leu Ala Ser Cys Ser Pro Glu Glu Ile Ile Glu
305                 310                 315                 320

Ala Ala Pro Ser Asp Lys Gln Ile Gln Trp Tyr Gln Leu Tyr Val Asn
                325                 330                 335

Ser Asp Arg Lys Ile Thr Asp Asp Leu Val Lys Asn Val Glu Lys Leu
            340                 345                 350

Gly Val Lys Ala Leu Phe Val Thr Val Asp Ala Pro Ser Leu Gly Gln
        355                 360                 365

Arg Glu Lys Asp Met Lys Leu Lys Phe Ser Asn Thr Lys Ala Gly Pro
    370                 375                 380

Lys Ala Met Lys Lys Thr Asn Val Glu Glu Ser Gln Gly Ala Ser Arg
385                 390                 395                 400

Ala Leu Ser Lys Phe Ile Asp Pro Ser Leu Thr Trp Lys Asp Ile Glu
                405                 410                 415

Glu Leu Lys Lys Lys Thr Lys Leu Pro Ile Val Ile Lys Gly Val Gln
            420                 425                 430

Arg Thr Glu Asp Val Ile Lys Ala Ala Glu Ile Gly Val Ser Gly Val
        435                 440                 445

Val Leu Ser Asn His Gly Gly Arg Gln Leu Asp Phe Ser Arg Ala Pro
    450                 455                 460

Ile Glu Val Leu Ala Glu Thr Met Pro Ile Leu Glu Gln Arg Asn Leu
465                 470                 475                 480

Lys Asp Lys Leu Glu Val Phe Val Asp Gly Gly Val Arg Arg Gly Thr
                485                 490                 495

Asp Val Leu Lys Ala Leu Cys Leu Gly Ala Lys Gly Val Gly Leu Gly
```

```
            500                 505                 510

Arg Pro Phe Leu Tyr Ala Asn Ser Cys Tyr Gly Arg Asn Gly Val Glu
        515                 520                 525

Lys Ala Ile Glu Ile Leu Arg Asp Glu Ile Glu Met Ser Met Arg Leu
    530                 535                 540

Leu Gly Val Thr Ser Ile Ala Glu Leu Lys Pro Asp Leu Leu Asp Leu
545                 550                 555                 560

Ser Thr Leu Lys Ala Arg Thr Val Gly Val Pro Asn Asp Val Leu Tyr
                565                 570                 575

Asn Glu Val Tyr Glu Gly Pro Thr Leu Thr Glu Phe Glu Asp Ala
            580                 585                 590


<210> SEQ ID NO 17
<211> LENGTH: 1776
<212> TYPE: DNA
<213> ORGANISM: Saccharomyces cerevisiae

<400> SEQUENCE: 17

atgctaaaat acaaaccttt actaaaaatc tcgaagaact gtgaggctgc tatcctcaga     60

gcgtctaaga ctagattgaa cacaatccgc gcgtacggtt ctaccgttcc aaaatccaag    120

tcgttcgaac aagactcaag aaaacgcaca cagtcatgga ctgccttgag agtcggtgca    180

attctagccg ctactagttc cgtggcgtat ctaaactggc ataatggcca aatagacaac    240

gagccgaaac tggatatgaa taaacaaaag atttcgcccg ctgaagttgc caagcataac    300

aagcccgatg attgttgggt tgtgatcaat ggttacgtat acgacttaac gcgattccta    360

ccaaatcatc caggtgggca ggatgttatc aagtttaacg ccgggaaaga tgtcactgct    420

atttttgaac cactacatgc tcctaatgtc atcgataagt atatagctcc cgagaaaaaa    480

ttgggtcccc ttcaaggatc catgcctcct gaacttgtct gtcctcctta tgctcctggt    540

gaaactaagg aagatatcgc tagaaaagaa caactaaaat cgctgctacc tcctctagat    600

aatattatta acctttacga ctttgaatac ttggcctctc aaactttgac taaacaagcg    660

tgggcctact attcctccgg tgctaacgac gaagttactc acagagaaaa ccataatgct    720

tatcatagga ttttttttcaa accaaagatc cttgtagatg tacgcaaagt agacatttca    780

actgacatgt tgggttctca tgtggatgtt cccttctacg tgtctgctac agctttgtgt    840

aaactgggaa acccccttaga aggtgaaaaa gatgtcgcca gaggttgtgg ccaaggtgtg    900

acaaaagtcc cacaaatgat atctactttg gcttcatgtt cccctgagga aattattgaa    960

gcagcaccct ctgataaaca aattcaatgg taccaactat atgttaactc tgatagaaag   1020

atcactgatg atttggttaa aaatgtagaa aagctgggtg taaaggcatt atttgtcact   1080

gtggatgctc caagtttagg tcaaagagaa aaagatatga agctgaaatt ttccaataca   1140

aaggctggtc caaaagcgat gaagaaaact aatgtagaag aatctcaagg tgcttcgaga   1200

gcgttatcaa agtttattga cccctctttg acttggaaag atatagaaga gttgaagaaa   1260

aagacaaaac tacctattgt tatcaaaggt gttcaacgta ccgaagatgt tatcaaagca   1320

gcagaaatcg gtgtaagtgg ggtggttcta tccaatcatg gtggtagaca attagatttt   1380

tcaagggctc ccattgaagt cctggctgaa accatgccaa tcctggaaca acgtaacttg   1440

aaggataagt tggaagtttt cgtggacggt ggtgttcgtc gtggtacaga tgtcttgaaa   1500

gcgttatgtc taggtgctaa aggtgttggt ttgggtagac cattcttgta tgcgaactca   1560

tgctatggtc gtaatggtgt tgaaaaagcc attgaaattt taagagatga aattgaaatg   1620
```

```
tctatgagac tattaggtgt tactagcatt gcggaattga agcctgatct tttagatcta   1680

tcaacactaa aggcaagaac agttggagta ccaaacgacg tgctgtataa tgaagtttat   1740

gagggaccta ctttaacaga atttgaggat gcatga                             1776


<210> SEQ ID NO 18
<211> LENGTH: 391
<212> TYPE: PRT
<213> ORGANISM: Saccharomyces cerevisiae

<400> SEQUENCE: 18

Met Ser Ala Ala Ala Asp Arg Leu Asn Leu Thr Ser Gly His Leu Asn
 1               5                  10                  15

Ala Gly Arg Lys Arg Ser Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
                325                 330                 335

Ser Ala Gln Gly Leu Ile Thr Cys Lys Glu Val His Glu Trp Leu Glu
            340                 345                 350
```

```
Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390


<210> SEQ ID NO 19
<211> LENGTH: 1176
<212> TYPE: DNA
<213> ORGANISM: Saccharomyces cerevisiae

<400> SEQUENCE: 19

atgtctgctg ctgctgatag attaaactta acttccggcc acttgaatgc tggtagaaag      60

agaagttcct cttctgtttc tttgaaggct gccgaaaagc ctttcaaggt tactgtgatt     120

ggatctggta actggggtac tactattgcc aaggtggttg ccgaaaattg taagggatac     180

ccagaagttt tcgctccaat agtacaaatg tgggtgttcg aagaagagat caatggtgaa     240

aaattgactg aaatcataaa tactagacat caaaacgtga aatacttgcc tggcatcact     300

ctacccgaca atttggttgc taatccagac ttgattgatt cagtcaagga tgtcgacatc     360

atcgttttca acattccaca tcaatttttg ccccgtatct gtagccaatt gaaaggtcat     420

gttgattcac acgtcagagc tatctcctgt ctaaagggtt ttgaagttgg tgctaaaggt     480

gtccaattgc tatcctctta catcactgag gaactaggta ttcaatgtgg tgctctatct     540

ggtgctaaca ttgccaccga agtcgctcaa gaacactggt ctgaaacaac agttgcttac     600

cacattccaa aggatttcag aggcgagggc aaggacgtcg accataaggt tctaaaggcc     660

ttgttccaca gaccttactt ccacgttagt gtcatcgaag atgttgctgg tatctccatc     720

tgtggtgctt tgaagaacgt tgttgcctta ggttgtggtt tcgtcgaagg tctaggctgg     780

ggtaacaacg cttctgctgc catccaaaga gtcggtttgg gtgagatcat cagattcggt     840

caaatgtttt tcccagaatc tagagaagaa acatactacc aagagtctgc tggtgttgct     900

gatttgatca ccacctgcgc tggtggtaga aacgtcaagg ttgctaggct aatggctact     960

tctggtaagg acgcctggga atgtgaaaag gagttgttga atggccaatc cgctcaaggt    1020

ttaattacct gcaaagaagt tcacgaatgg ttggaaacat gtggctctgt cgaagacttc    1080

ccattatttg aagccgtata ccaaatcgtt tacaacaact acccaatgaa gaacctgccg    1140

gacatgattg aagaattaga tctacatgaa gattag                              1176


<210> SEQ ID NO 20
<211> LENGTH: 332
<212> TYPE: PRT
<213> ORGANISM: Pelodiscus sinensis japonicus

<400> SEQUENCE: 20

Met Ser Val Lys Glu Leu Leu Ile Gln Asn Val His Lys Glu Glu His
 1               5                  10                  15

Ser His Ala His Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Arg Gly Glu Met Leu Asp
    50                  55                  60

Leu Gln His Gly Ser Leu Phe Leu Arg Thr Pro Lys Ile Val Ser Gly
```

```
65                  70                  75                  80

Lys Asp Tyr Ser Val Thr Ala His Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Asp Cys Met Leu Leu Val Val Ser Asn Pro Val Asp Ile Leu Thr
    130                 135                 140

Tyr Val Ala Trp Lys Ile Ser Gly Phe Pro Lys His Arg Val Ile Gly
145                 150                 155                 160

Ser Gly Cys Asn Leu Asp Ser Ala Arg Phe Arg Tyr Leu Met Gly Glu
                165                 170                 175

Lys Leu Gly Ile His Ser Leu Ser Cys His Gly Trp Ile Ile Gly Glu
            180                 185                 190

His Gly Asp Ser Ser Val Pro Val Trp Ser Gly Val Asn Val Ala Gly
        195                 200                 205

Val Ser Leu Lys Ala Leu Tyr Pro Asp Leu Gly Thr Asp Ala Asp Lys
    210                 215                 220

Glu His Trp Lys Glu Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Thr Val Met Lys Asn Leu Arg Arg Val His Pro
            260                 265                 270

Ile Ser Thr Met Val Lys Gly Met Tyr Gly Val Ser Ser Asp Val Phe
        275                 280                 285

Leu Ser Val Pro Cys Val Leu Gly Tyr Ala Gly Ile Thr Asp Val Val
    290                 295                 300

Lys Met Thr Leu Lys Ser Glu Glu Glu Glu Lys Leu Arg Lys Ser Ala
305                 310                 315                 320

Asp Thr Leu Trp Gly Ile Gln Lys Glu Leu Gln Phe
                325                 330


<210> SEQ ID NO 21
<211> LENGTH: 332
<212> TYPE: PRT
<213> ORGANISM: Ornithorhynchus anatinus

<400> SEQUENCE: 21

Met Ala Gly Val Lys Glu Gln Leu Ile Gln Asn Leu Leu Lys Glu Glu
 1               5                  10                  15

Tyr Ala Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Lys Gly Glu Met Met Asp
    50                  55                  60

Leu Gln His Gly Ser Leu Phe Leu Arg Thr Pro Lys Ile Val Ser Gly
65                  70                  75                  80

Lys Asp Tyr Ser Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110
```

```
Asn Val Asn Ile Phe Lys Phe Ile Ile Pro Asn Val Val Lys Tyr Ser
        115                 120                 125

Pro Asn Cys Lys Leu Leu Val Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Ile His Ser Thr Ser Cys His Gly Trp Val Ile Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Asp Leu Gly Thr Asp Ala Asp Lys
    210                 215                 220

Glu Gln Trp Lys Asp Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Val Lys Asn Leu Arg Arg Val His Pro
            260                 265                 270

Ile Ser Thr Met Ile Lys Gly Leu Tyr Gly Ile Lys Asp Glu Val Phe
        275                 280                 285

Leu Ser Val Pro Cys Val Leu Gly Gln Asn Gly Ile Ser Asp Val Val
    290                 295                 300

Lys Ile Thr Leu Lys Ser Glu Glu Glu Ala His Leu Lys Lys Ser Ala
305                 310                 315                 320

Asp Thr Leu Trp Gly Ile Gln Lys Glu Leu Gln Phe
                325                 330


<210> SEQ ID NO 22
<211> LENGTH: 332
<212> TYPE: PRT
<213> ORGANISM: Tursiops truncatus

<400> SEQUENCE: 22

Met Ala Thr Val Lys Asp Gln Leu Ile Gln Asn Leu Leu Lys Glu Glu
 1               5                  10                  15

His Val Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Lys Gly Glu Met Met Asp
    50                  55                  60

Leu Gln His Gly Ser Leu Phe Leu Arg Thr Pro Lys Ile Val Ser Gly
65                  70                  75                  80

Lys Asp Tyr Ser Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Val Pro Asn Ile Val Lys Tyr Ser
        115                 120                 125

Pro His Cys Lys Leu Leu Val Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160
```

```
Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Ile Leu Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Glu Leu Gly Thr Asp Ala Asp Lys
    210                 215                 220

Glu His Trp Lys Ala Ile His Lys Gln Val Val Asp Ser Ala Tyr Glu
225                 230                 235                 240

Val Ile Lys Leu Lys Gly Tyr Thr Ser Trp Ala Val Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
    290                 295                 300

Lys Val Thr Leu Thr Pro Glu Glu Gln Ala Cys Leu Lys Lys Ser Ala
305                 310                 315                 320

Asp Thr Leu Trp Gly Ile Gln Lys Glu Leu Gln Phe
                325                 330


<210> SEQ ID NO 23
<211> LENGTH: 332
<212> TYPE: PRT
<213> ORGANISM: Rattus norvegicus

<400> SEQUENCE: 23

Met Ala Ala Leu Lys Asp Gln Leu Ile Val Asn Leu Leu Lys Glu Glu
1               5                   10                  15

Gln Val Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Lys Gly Glu Met Met Asp
    50                  55                  60

Leu Gln His Gly Ser Leu Phe Leu Lys Thr Pro Lys Ile Val Ser Ser
65                  70                  75                  80

Lys Asp Tyr Ser Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Gln Cys Lys Leu Leu Ile Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Val Leu Gly Glu
            180                 185                 190

His Gly Asp Ser Ser Val Pro Val Trp Ser Gly Val Asn Val Ala Gly
```

```
        195                 200                 205

Val Ser Leu Lys Ser Leu Asn Pro Gln Leu Gly Thr Asp Ala Asp Lys
    210                 215                 220

Glu Gln Trp Lys Asp Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
    290                 295                 300

Lys Val Thr Leu Thr Pro Asp Glu Glu Ala Arg Leu Lys Lys Ser Ala
305                 310                 315                 320

Asp Thr Leu Trp Gly Ile Gln Lys Glu Leu Gln Phe
                325                 330
```

<210> SEQ ID NO 24
<211> LENGTH: 999
<212> TYPE: DNA
<213> ORGANISM: Pelodiscus sinensis japonicus

<400> SEQUENCE: 24

```
atgtccgtaa aggaactact tatacaaaac gtccataagg aggagcattc tcacgctcac      60

aataagataa cagttgtagg agtaggtgca gtaggtatgg catgtgctat ttcgatatta     120

atgaaagact tggctgatga actagccttg gttgatgtga ttgaggataa gttacgtgga     180

gaaatgttag atttgcaaca tggttcattg ttcttgagaa cccccaaaat tgtctcgggt     240

aaggattatt cagtcactgc tcattctaaa ctggttatca ttacagcagg tgcaagacag     300

caagaagggg agagcagact aaatctggtt caacgtaatg tcaacatctt caagtttatc     360

atcccgaacg tagtaaaata cagtccagac tgcatgttgc ttgttgtgag taatccagtt     420

gacatcttaa cctatgttgc gtggaaaatc agtgggtttc caaaacatag ggtgattggc     480

tcaggatgca accttgatag cgccaggttt aggtatctaa tgggagaaaa attaggtatt     540

cactccttat cttgtcatgg ctggataata ggcgaacatg gtgattcttc ggtacctgtt     600

tggtccgggg ttaatgtggc tggtgttagt ttaaaagcat tatatcctga cctgggtact     660

gatgccgata aagaacattg gaaagaagtg cacaaacaag tggttgattc tgcttacgaa     720

gttattaaac ttaagggcta cacttcttgg gctataggtc tatcagtagc tgatttggca     780

gaaaccgtta tgaaaaattt aagaagagtc cacccaattt ccacgatggt caagggtatg     840

tacggtgtta gctctgacgt cttcttatct gttccttgtg ttttgggata tgcgggaatt     900

acagacgtcg tgaagatgac attgaaatca gaggaagagg aaaaactaag aaagtcagcc     960

gatactctgt ggggcattca aaaggaattg cagttttaa                            999
```

<210> SEQ ID NO 25
<211> LENGTH: 1267
<212> TYPE: DNA
<213> ORGANISM: Artificial Sequence
<220> FEATURE:
<223> OTHER INFORMATION: Synthetic (ARS/CEN)

<400> SEQUENCE: 25

```
gagctccttt catttctgat aaaagtaaga ttactccatt tatcttttca ccaacatatt      60
```

```
catagttgaa agttatcctt ctaagtacgt atacaatatt aattaaacgt aaaaacaaaa    120

ctgactgtaa aaatgtgtaa aaaaaaaata tcaaattcat agcagtttca aggaatgaaa    180

actattatga tctggtcacg tgtatataaa ttattaattt taaacccata taatttatta    240

ttttttttatt ctaaagttta aagtaatttt agtagtattt tatattttga ataaatatac   300

tttaaatttt tatttttata ttttattact tttaaaaata atgtttttat ttaaaacaaa    360

attataagtt aaaaagttgt tccgaaagta aaatatattt tatagttttt acaaaaataa    420

attattttta acgtattttt tttaattata tttttgtatg tgattatatc cacaggtatt    480

atgctgaatt tagctgtttc agtttaccag tgtgatagta tgattttttt tgcctctcaa    540

aagctatttt tttagaagct tcgtcttaga aataggtggt gtataaattg cggttgactt    600

ttaactatat atcattttcg atttatttat tacatagaga ggtgctttta attttttaat    660

ttttattttc aataatttta aaagtgggta cttttaaatt ggaacaaagt gaaaaatatc    720

tgttatacgt gcaactgaat ttactgacc ttaaaggact atctcaatcc tggttcagaa     780

atccttgaaa tgattgatat gttggtggat tttctctgat tttcaaacaa gaggtatttt    840

atttcatatt tattatattt tttacattta ttttatattt ttttattgtt tggaagggaa    900

agcgacaatc aaattcaaaa tatattaatt aaactgtaat acttaataag agacaaataa    960

cagccaagaa tcaaatactg ggtttttaat caaaagatct ctctacatgc acccaaattc   1020

attatttaaa tttactatac tacagacaga atatacgaac ccagattaag tagtcagacg   1080

cttttccgct ttattgagta tatagcctta catattttct gcccataatt tctggattta   1140

aaataaacaa aaatggttac tttgtagtta tgaaaaaagg cttttccaaa atgcgaaata   1200

cgtgttattt aaggttaatc aacaaaacgc atatccatat gggtagttgg acaaaacttc   1260

aatcgat                                                             1267
```

<210> SEQ ID NO 26
<211> LENGTH: 289
<212> TYPE: DNA
<213> ORGANISM: Artificial Sequence
<220> FEATURE:
<223> OTHER INFORMATION: Synthetic (CYC promoter)

<400> SEQUENCE: 26

```
atttggcgag cgttggttgg tggatcaagc ccacgcgtag gcaatcctcg agcagatccg     60

ccaggcgtgt atatatagcg tggatggcca ggcaacttta gtgctgacac atacaggcat    120

atatatatgt gtgcgacgac acatgatcat atggcatgca tgtgctctgt atgtatataa    180

aactcttgtt ttcttctttt ctctaaatat tctttcctta tacattagga cctttgcagc    240

ataaattact atacttctat agacacgcaa acacaaatac acacactaa               289
```

<210> SEQ ID NO 27
<211> LENGTH: 401
<212> TYPE: DNA
<213> ORGANISM: Artificial Sequence
<220> FEATURE:
<223> OTHER INFORMATION: Synthetic (TEF promoter)

<400> SEQUENCE: 27

```
atagcttcaa aatgtttcta ctcctttttt actcttccag attttctcgg actccgcgca     60

tcgccgtacc acttcaaaac acccaagcac agcatactaa atttcccctc tttcttcctc    120

tagggtgtcg ttaattaccc gtactaaagg tttggaaaag aaaaaagaga ccgcctcgtt    180
```

tctttttctt cgtcgaaaaa ggcaataaaa atttttatca cgtttctttt tcttgaaaat 240 ttttttttg attttttct ctttcgatga cctcccattg atatttaagt taataaacgg 300
tcttcaattt ctcaagtttc agtttcattt ttcttgttct attacaactt tttttacttc 360
ttgctcatta gaaagaaagc atagcaatct aatctaagtt t 401

<210> SEQ ID NO 28
<211> LENGTH: 655
<212> TYPE: DNA
<213> ORGANISM: Artificial Sequence
<220> FEATURE:
<223> OTHER INFORMATION: Synthetic (GPD promoter)

<400> SEQUENCE: 28
agtttatcat tatcaatact cgccatttca aagaatacgt aaataattaa tagtagtgat 60
tttcctaact ttatttagtc aaaaaattag ccttttaatt ctgctgtaac ccgtacatgc 120
ccaaaatagg gggcgggtta cacagaatat ataacatcgt aggtgtctgg gtgaacagtt 180
tattcctggc atccactaaa tataatggag cccgcttttt aagctggcat ccagaaaaaa 240
aaagaatccc agcaccaaaa tattgttttc ttcaccaacc atcagttcat aggtccattc 300
tcttagcgca actacagaga acaggggcac aaacaggcaa aaaacgggca caacctcaat 360
ggagtgatgc aacctgcctg gagtaaatga tgacacaagg caattgaccc acgcatgtat 420
ctatctcatt ttcttacacc ttctattacc ttctgctctc tctgatttgg aaaaagctga 480
aaaaaaaggt tgaaaccagt tccctgaaat tattccccta cttgactaat aagtatataa 540
agacggtagg tattgattgt aattctgtaa atctatttct taaacttctt aaattctact 600
tttatagtta gtcttttttt tagttttaaa acaccagaac ttagtttcga cggat 655

<210> SEQ ID NO 29
<211> LENGTH: 1468
<212> TYPE: DNA
<213> ORGANISM: Artificial Sequence
<220> FEATURE:
<223> OTHER INFORMATION: Synthetic (ADH promoter)

<400> SEQUENCE: 29
gccgggatcg aagaaatgat ggtaaatgaa ataggaaatc aaggagcatg aaggcaaaag 60
acaaatataa gggtcgaacg aaaaataaag tgaaaagtgt tgatatgatg tatttggctt 120
tgcggcgccg aaaaaacgag tttacgcaat tgcacaatca tgctgactct gtggcggacc 180
cgcgctcttg ccggcccggc gataacgctg ggcgtgaggc tgtgcccggc ggagtttttt 240
gcgcctgcat ttccaaggt ttaccctgcg ctaaggggcg agattggaga agcaataaga 300
atgccggttg gggttgcgat gatgacgacc acgacaactg gtgtcattat ttaagttgcc 360
gaaagaacct gagtgcattt gcaacatgag tatactagaa gaatgagcca agacttgcga 420
gacgcgagtt tgccggtggt gcgaacaata gagcgaccat gaccttgaag gtgagacgcg 480
cataaccgct agagtacttt gaagaggaaa cagcaatagg gttgctacca gtataaatag 540
acaggtacat acaacactgg aaatggttgt ctgtttgagt acgctttcaa ttcatttggg 600
tgtgcacttt attatgttac aatatggaag ggaactttac acttctccta tgcacatata 660
ttaattaaag tccaatgcta gtagagaagg ggggtaacac ccctccgcgc tcttttccga 720
tttttttcta aaccgtggaa tatttcggat atccttttgt tgtttccggg tgtacaatat 780
ggacttcctc ttttctggca accaaaccca tacatcggga ttcctataat accttcgttg 840
gtctccctaa catgtaggtg gcggaggga gatatacaat agaacagata ccagacaaga 900

```
cataatgggc taaacaagac tacaccaatt acactgcctc attgatggtg gtacataacg    960

aactaatact gtagccctag acttgatagc catcatcata tcgaagtttc actacccttt   1020

ttccatttgc catctattga agtaataata ggcgcatgca acttcttttc tttttttttc   1080

ttttctctct cccccgttgt tgtctcacca tatccgcaat gacaaaaaaa tgatggaaga   1140

cactaaagga aaaaattaac gacaaagaca gcaccaacag atgtcgttgt tccagagctg   1200

atgaggggta tctcgaagca cacgaaactt tttccttcct tcattcacgc acactactct   1260

ctaatgagca acggtatacg gccttccttc cagttacttg aatttgaaat aaaaaaaagt   1320

ttgctgtctt gctatcaagt ataaatagac ctgcaattat taatcttttg tttcctcgtc   1380

attgttctcg ttccctttct tccttgtttc tttttctgca caatatttca agctatacca   1440

agcatacaat caactccaag ctggccgc                                      1468


<210> SEQ ID NO 30
<211> LENGTH: 252
<212> TYPE: DNA
<213> ORGANISM: Artificial Sequence
<220> FEATURE:
<223> OTHER INFORMATION: Synthetic (CYC1 terminator)

<400> SEQUENCE: 30

tcatgtaatt agttatgtca cgcttacatt cacgccctcc ccccacatcc gctctaaccg     60

aaaaggaagg agttagacaa cctgaagtct aggtccctat ttattttttt atagttatgt    120

tagtattaag aacgttattt atatttcaaa tttttctttt ttttctgtac agacgcgtgt    180

acgcatgtaa cattatactg aaaaccttgc ttgagaaggt tttgggacgc tcgaaggctt    240

taatttgcgg cc                                                        252


<210> SEQ ID NO 31
<211> LENGTH: 31
<212> TYPE: DNA
<213> ORGANISM: Artificial Sequence
<220> FEATURE:
<223> OTHER INFORMATION: Synthetic (forward primer)

<400> SEQUENCE: 31

cgagctcttc gcggccacct acgccgctat c                                    31


<210> SEQ ID NO 32
<211> LENGTH: 32
<212> TYPE: DNA
<213> ORGANISM: Artificial Sequence
<220> FEATURE:
<223> OTHER INFORMATION: Synthetic (reverse primer)

<400> SEQUENCE: 32

gctctagata ttgatatagt gtttaagcga at                                   32


<210> SEQ ID NO 33
<211> LENGTH: 26
<212> TYPE: DNA
<213> ORGANISM: Artificial Sequence
<220> FEATURE:
<223> OTHER INFORMATION: Synthetic (forward primer)

<400> SEQUENCE: 33

ggatccatgt ccgtaaagga actact                                          26


<210> SEQ ID NO 34
```

```
<211> LENGTH: 34
<212> TYPE: DNA
<213> ORGANISM: Artificial Sequence
<220> FEATURE:
<223> OTHER INFORMATION: Synthetic (reverse primer)

<400> SEQUENCE: 34

acgcgtcgac ttaaaactgc aattcctttt gaat                              34


<210> SEQ ID NO 35
<211> LENGTH: 26
<212> TYPE: DNA
<213> ORGANISM: Artificial Sequence
<220> FEATURE:
<223> OTHER INFORMATION: Synthetic (forward primer)

<400> SEQUENCE: 35

gagctcaatt aaccctcact aaaggg                                       26


<210> SEQ ID NO 36
<211> LENGTH: 26
<212> TYPE: DNA
<213> ORGANISM: Artificial Sequence
<220> FEATURE:
<223> OTHER INFORMATION: Synthetic (reverse primer)

<400> SEQUENCE: 36

gagctccaaa ttaaagcctt cgagcg                                       26


<210> SEQ ID NO 37
<211> LENGTH: 60
<212> TYPE: DNA
<213> ORGANISM: Artificial Sequence
<220> FEATURE:
<223> OTHER INFORMATION: Synthetic (forward primer)

<400> SEQUENCE: 37

aagatctacg aagttgaagg tatgagatgg gctggtaacg ccagtcacga cgttgtaaaa     60


<210> SEQ ID NO 38
<211> LENGTH: 60
<212> TYPE: DNA
<213> ORGANISM: Artificial Sequence
<220> FEATURE:
<223> OTHER INFORMATION: Synthetic (reverse primer)

<400> SEQUENCE: 38

gcttccttaa cttctggctt ggacaaggta ccgacgtaaa aggtttcccg actggaaagc     60


<210> SEQ ID NO 39
<211> LENGTH: 70
<212> TYPE: DNA
<213> ORGANISM: Artificial Sequence
<220> FEATURE:
<223> OTHER INFORMATION: Synthetic (forward primer)

<400> SEQUENCE: 39

cgatgcgtat tttaagtggt tctctgaaca gcacaatgtc ctcgacacca ccagtcacga     60

cgttgtaaaa                                                         70


<210> SEQ ID NO 40
<211> LENGTH: 72
<212> TYPE: DNA
<213> ORGANISM: Artificial Sequence
<220> FEATURE:
<223> OTHER INFORMATION: Synthetic (reverse primer)
```

<400> SEQUENCE: 40
ggatcacccc ccactcaagt cgttgcattg ctaacatgtg gcattctgcc caaggtttcc 60
cgactggaaa gc 72

<210> SEQ ID NO 41
<211> LENGTH: 70
<212> TYPE: DNA
<213> ORGANISM: Artificial Sequence
<220> FEATURE:
<223> OTHER INFORMATION: Synthetic (forward primer)

<400> SEQUENCE: 41
ccctatgtct ctggccgatc acgcgccatt gtccctcaga aacaaatcaa ccagtcacga 60
cgttgtaaaa 70

<210> SEQ ID NO 42
<211> LENGTH: 70
<212> TYPE: DNA
<213> ORGANISM: Artificial Sequence
<220> FEATURE:
<223> OTHER INFORMATION: Synthetic (reverse primer)

<400> SEQUENCE: 42
tagaagcaac tgtgccgaca gcctctgaat gagtggtgtt gtaaccaccc aggtttcccg 60
actggaaagc 70

<210> SEQ ID NO 43
<211> LENGTH: 22
<212> TYPE: DNA
<213> ORGANISM: Artificial Sequence
<220> FEATURE:
<223> OTHER INFORMATION: Synthetic (forward primer)

<400> SEQUENCE: 43
gctcttctct accctgtcat tc 22

<210> SEQ ID NO 44
<211> LENGTH: 22
<212> TYPE: DNA
<213> ORGANISM: Artificial Sequence
<220> FEATURE:
<223> OTHER INFORMATION: Synthetic (reverse primer)

<400> SEQUENCE: 44
tagtgtacag ggtgtcgtat ct 22

<210> SEQ ID NO 45
<211> LENGTH: 26
<212> TYPE: DNA
<213> ORGANISM: Artificial Sequence
<220> FEATURE:
<223> OTHER INFORMATION: Synthetic (forward primer)

<400> SEQUENCE: 45
ggagttgaag gcaaaattag aagtga 26

<210> SEQ ID NO 46
<211> LENGTH: 26
<212> TYPE: DNA
<213> ORGANISM: Artificial Sequence
<220> FEATURE:
<223> OTHER INFORMATION: Synthetic (reverse primer)

<400> SEQUENCE: 46
attccctttc ctgcacaaca cgagat 26

<210> SEQ ID NO 47
<211> LENGTH: 25
<212> TYPE: DNA
<213> ORGANISM: Artificial Sequence
<220> FEATURE:
<223> OTHER INFORMATION: Synthetic (forward primer)

<400> SEQUENCE: 47
tcaatgagac tgttgtcctc ctact 25

<210> SEQ ID NO 48
<211> LENGTH: 24
<212> TYPE: DNA
<213> ORGANISM: Artificial Sequence
<220> FEATURE:
<223> OTHER INFORMATION: Synthetic (reverse primer)

<400> SEQUENCE: 48
tacatccttg tcgagccttg ggca 24

<210> SEQ ID NO 49
<211> LENGTH: 34
<212> TYPE: DNA
<213> ORGANISM: Artificial Sequence
<220> FEATURE:
<223> OTHER INFORMATION: Synthetic (forward primer)

<400> SEQUENCE: 49
cgcggatcca tggctagaac tttctttgtc ggtg 34

<210> SEQ ID NO 50
<211> LENGTH: 35
<212> TYPE: DNA
<213> ORGANISM: Artificial Sequence
<220> FEATURE:
<223> OTHER INFORMATION: Synthetic (reverse primer)

<400> SEQUENCE: 50
acgcgtcgac ttagtttcta gagttgatga tatca 35

<210> SEQ ID NO 51
<211> LENGTH: 29
<212> TYPE: DNA
<213> ORGANISM: Artificial Sequence
<220> FEATURE:
<223> OTHER INFORMATION: Synthetic (forward primer)

<400> SEQUENCE: 51
cgcggatcca tgtcaaaacc gcaacccat 29

<210> SEQ ID NO 52
<211> LENGTH: 30
<212> TYPE: DNA
<213> ORGANISM: Artificial Sequence
<220> FEATURE:
<223> OTHER INFORMATION: Synthetic (reverse primer)

<400> SEQUENCE: 52
acgcgtcgac ttactgagta gcttttatga 30

<210> SEQ ID NO 53
<211> LENGTH: 29

-continued

```
<212> TYPE: DNA
<213> ORGANISM: Artificial Sequence
<220> FEATURE:
<223> OTHER INFORMATION: Synthetic (forward primer)

<400> SEQUENCE: 53

cgcggatcca tggctccctc aagaaagtt                                      29


<210> SEQ ID NO 54
<211> LENGTH: 30
<212> TYPE: DNA
<213> ORGANISM: Artificial Sequence
<220> FEATURE:
<223> OTHER INFORMATION: Synthetic (reverse primer)

<400> SEQUENCE: 54

acgcgtcgac ttattgctta gcatttatga                                     30
```